(12) United States Patent
Andrean et al.

(10) Patent No.: US 6,635,090 B1
(45) Date of Patent: Oct. 21, 2003

(54) DYEING METHOD USING A SPECIFIC CATIONIC DERIVATIVE AND A COMPOUND SELECTED AMONG A SPECIFIC ALDEHYDE, A SPECIFIC KETONE, A QUINONE AND A DI-IMINO-ISOINDOLINE OR 3-AMINO-ISOINDOLONE DERIVATIVE

(75) Inventors: Hervé Andrean, Paris (FR); Alain Lagrange, Coupvray (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/622,710

(22) PCT Filed: Dec. 22, 1999

(86) PCT No.: PCT/FR99/03246

§ 371 (c)(1),
(2), (4) Date: Oct. 3, 2000

(87) PCT Pub. No.: WO00/38639

PCT Pub. Date: Jul. 6, 2000

(30) Foreign Application Priority Data

Dec. 23, 1998 (FR) .............................. 98 16378

(51) Int. Cl.[7] .................................................. A61K 7/13
(52) U.S. Cl. ...................... 8/405; 8/406; 8/407; 8/408; 8/409; 546/298
(58) Field of Search ............................ 8/405, 406, 407, 8/408, 409; 546/298

(56) References Cited

U.S. PATENT DOCUMENTS

| 4,661,114 | A | * | 4/1987 | Konrad et al. | 8/409 |
|---|---|---|---|---|---|
| 4,695,285 | A | * | 9/1987 | Chung-Bong-Chan et al. | 8/429 |
| 4,931,066 | A | * | 6/1990 | Grollier et al. | 8/410 |
| 5,034,014 | A | * | 7/1991 | Wenke | 8/408 |
| 5,131,911 | A | * | 7/1992 | Lang et al. | 8/405 |
| 5,145,482 | A | * | 9/1992 | Clausen et al. | 8/409 |
| 5,279,616 | A | * | 1/1994 | Lang et al. | 8/406 |
| 5,340,366 | A | | 8/1994 | Lang et al. | 8/406 |
| 5,516,916 | A | * | 5/1996 | Murphy et al. | 548/509 |
| 5,518,505 | A | * | 5/1996 | Cotteret | 8/409 |
| 5,578,087 | A | * | 11/1996 | Audousset et al. | 8/409 |
| 5,616,150 | A | * | 4/1997 | Moeller et al. | 8/405 |
| 5,628,799 | A | * | 5/1997 | Wenke et al. | 8/407 |
| 5,752,982 | A | * | 5/1998 | Lang et al. | 8/409 |
| 5,769,903 | A | * | 6/1998 | Audousset et al. | 8/409 |
| 5,874,091 | A | * | 2/1999 | Grollier | 424/401 |
| 5,919,273 | A | * | 7/1999 | Rondeau et al. | 8/412 |
| 6,001,135 | A | * | 12/1999 | Rondeau et al. | 8/407 |
| 6,063,136 | A | * | 5/2000 | Vidal et al. | 8/409 |
| 6,201,125 | B1 | * | 3/2001 | Begley | 546/298 |
| 6,306,181 | B1 | * | 10/2001 | Terranova et al. | 8/409 |

FOREIGN PATENT DOCUMENTS

| EP | 0 502 783 | | 9/1992 | | |
|---|---|---|---|---|---|
| EP | 0 847 749 | | 6/1998 | | |
| EP | 847749 | * | 6/1998 | ............ | A61K/7/13 |
| EP | 0873744 | A2 * | 10/1998 | | |
| EP | 0 873 745 | | 10/1998 | | |
| GB | 2181750 | A * | 4/1987 | ............ | A61K/7/13 |
| WO | WO00/33799 | * | 6/2000 | | |

OTHER PUBLICATIONS

English language Derwent Abstract of EP 0 502 783.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

Compositions, methods, and kits for dyeing at least one keratin fiber, comprising at least one specific cationic compound and at least one compound chosen from specific aldehydes, specific ketones, quinones, diiminoisoindoline derivatives, and 3-aminoisoindolone derivatives, with the proviso that the inventive compositions do not comprise an oxidizing agent.

64 Claims, No Drawings

DYEING METHOD USING A SPECIFIC CATIONIC DERIVATIVE AND A COMPOUND SELECTED AMONG A SPECIFIC ALDEHYDE, A SPECIFIC KETONE, A QUINONE AND A DI-IMINO-ISOINDOLINE OR 3-AMINO-ISOINDOLONE DERIVATIVE

The present invention relates to the use, for dyeing keratin fibres, of at least one heterocyclic cationic amine and of at least one compound chosen from a specific aldehyde of formula (III) defined below, a specific ketone of formula (IV) or (V) defined below, a quinone and a diiminoisoindoline or 3-aminoisoindolone derivative, to dye compositions comprising a combination of these compounds, to dyeing processes using the said compounds and to a multi-compartment device containing these compounds.

It is known practice, for the dyeing of keratin fibres, and in particular of human keratin fibres such as the hair, to use direct dyes or coloured substances which give the fibre a temporary or semi-permanent coloration, of low dyeing power, which is generally removed by washing or by perspiration. The range of shades obtained by these direct processes is generally limited. It is also known practice to use oxidation dyes (oxidation bases and couplers), which are compounds which are initially colourless or weakly coloured and which, under the action of an oxidizing agent, generate coloured compounds by a process of oxidative condensation. Compared with direct colorations, oxidative colorations are permanent, powerful and withstand external agents (light, bad weather, washing, perspiration and rubbing). Nevertheless, the use of the oxidizing agent can harm the keratin fibres and make the processes for carrying out the oxidative dyeing operations relatively complex.

The Applicant has just discovered a novel dyeing process, which does not involve a process of oxidative development of dyes, and which gives a wide range of shades.

The compounds used by the Applicant are small molecules which can penetrate into keratin easily. The Applicant has found, surprisingly, that these compounds can then condense to form chromophores or dyes, bulkier molecules which remain trapped inside the keratin.

The Applicant has thus found that the dyes obtained withstand shampooing and perspiration and are stable with respect to light, bad weather and chemical agents. The Applicant has, in a way, discovered a novel dyeing process which has the advantages of so-called oxidation dyeing without exhibiting its drawbacks, since no oxidizing agent is used.

One subject of the present invention is thus the use, for dyeing keratin fibres, of a specific cationic derivative and of a compound chosen from an aldehyde of formula (III), a ketone of formula (IV) or (V), a quinone and a diiminoisoindoline or 3-amino-isoindolone derivative.

Another subject of the invention relates to dye compositions comprising these compounds.

A subject of the present invention is also a process for dyeing keratin fibres, which consists in applying a specific cationic derivative and a compound chosen from an aldehyde of formula (III), a ketone of formula (IV) or (V), a quinone and a diiminoisoindoline or 3-aminoisoindolone derivative to the fibres, either simultaneously, in the form of a mixture prepared at the time of use, or successively.

Another subject of the invention also consists of a dyeing agent for carrying out the process of the invention.

Other subjects of the invention will become apparent in the light of the description.

The main subject of the present invention is thus the use, for dyeing keratin fibres, in particular human keratin fibres such as the hair, of at least one specific cationic derivative and of at least one compound chosen from an aldehyde of formula (III), a ketone of formula (IV) or (V), a quinone and a diiminoisoindoline or 3-aminoisoindolone derivative, in order to obtain, by reaction without an oxidizing agent, a coloration of the said keratin fibres.

In the context of the present invention, the cationic derivatives are chosen from:

the compounds of formula (I) below:

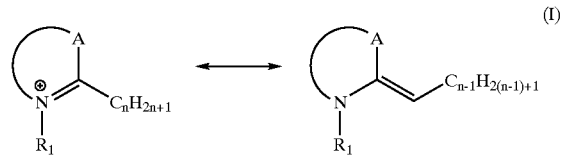

in which:

n denotes an integer from 1 to 4;

$R_1$ denotes an alkyl, hydroxyalkyl, polyhydroxyalkyl, alkylhydroxyalkyl, alkylsulphonyl, carboxyalkyl, aminoalkyl, (dihydroxy)alkylaminoalkyl, alkyl-NR'R" (in which R' and R" are alkyl or can form, together with the nitrogen atom to which they are attached, a 5- or 6-membered aliphatic or heterocyclic ring) or an aryl radical, the alkyl radicals of the groups defined above containing from 1 to 4 carbon atoms and being linear or branched;

A and the nitrogen together form an unsaturated, aromatic or heterocyclic, 5- or 6-membered hydrocarbon-based ring which may be interrupted with one or more nitrogen, oxygen or sulphur atoms and which may be substituted with one or more radicals such as —$NO_2$, —$NH_2$, acetylamino, —OH, —$SO_3H$, a halogen atom, —$CH_3SO_2$, —$CF_3$, $C_1$–$C_4$ alkyl, $C_1$–$C_4$ alkoxy, $C_1$–$C_4$ alkylthio and ($C_1$–$C_4$) alkoxycarbonyl, A denotes a substituted or unsubstituted carbon, a substituted or unsubstituted nitrogen, an oxygen or a sulphur;

the 5- or 6-membered hydrocarbon-based ring formed by A and the nitrogen can also be fused with a substituted or unsubstituted aromatic ring such as, in particular, aryl or naphthyl substituted with one or more halogen, allyl or alkoxy radicals;

or the compounds of formula (II) below:

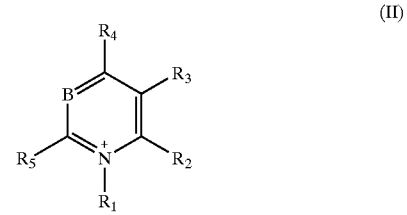

in which:

$R_1$ is defined as above, $R_2$, $R_3$, $R_4$ or $R_5$, which may be identical or different, denote the substituents denoted by $R_1$;

B denotes —CH— or a nitrogen;

the groups $R_1$ and $R_2$, $R_2$ and $R_3$, $R_3$ and $R_4$, $R_5$ and $R_1$, the group $R_5$ or $R_4$ and B can form, together with the atoms to which they are attached, an unsaturated, aromatic or heterocyclic, 5- or 6-membered hydrocarbon-based ring which may be interrupted with one or more nitrogen or sulphur atoms and which may be substituted with one or more radicals such as —$NO_2$, —$NH_2$, acetylamino, —OH, —$SO_3H$, a halogen atom, —$CH_3SO_2$, —$CF_3$, —$OCF_3$, $C_1$–$C_4$ alkyl, $C_1$–$C_4$ alkoxy, $C_1$–$C_4$ alkylthio and ($C_1$–$C_4$)alkoxycarbonyl and the cosmetically acceptable salts of these compounds.

The compounds of formula (I) are chosen in particular from the following compounds:

1,2,3-trimethyl-3H-imidazol-1-ium iodide
2,3,4-trimethylthiazol-3-ium iodide
3-ethylmethylbenzothiazolium iodide
3-methylmethylbenzothiazolium methosulphate
1,2,3,3-tetramethyl-3H-indolium iodide
3-ethylmethylbenzoxazolium iodide
1,2,3-trimethyl-3H-imidazol-1-ium methosulphate
3-(2-carboxyethyl)-2,5-dimethylbenzoxazol-3-ium bromide
3-ethylmethylbenzothiazolium toluene-4-sulphonate
5-chloro-3-ethyl-2-methylbenzothiazol-3-ium toluene-4-sulphonate
1-ethyl-2-methylnaphtho[1,2-d]thiazol-1-ium toluene-4-sulphonate
1,2,3-trimethyl-3H-benzoimidazol-1-ium tetrafluoroborate
2-ethyl-3-methylbenzo[d]isothiazol-2-ium tetrafluoroborate
2-methyl-3-(3-sulphonatopropyl)benzothiazol-3-ium
3-tertbutyl-2-methylbenzothiazol-3-ium bromide
3-(2-carboxyethyl)-2,5-dimethylbenzoxazol-3-ium bromide
5-methoxy-2-methyl-3-(3-sulphonatopropyl)benzothiazol-3-ium
2-methyl-1-(3-sulphonatopropyl)naphtho[1,2-d]oxazol-1-ium
2-methyl-3-(3-sulphonatopropyl)naphtho[2,3-d]oxazol-3-ium
2,5,6-trimethyl-3-(3-sulphonatopropyl)thieno[2,3-d]-thiazol-3-ium
1-ethyl-2-methylnaphtho1,2-dioxazol-1-ium perchlorate;
1,2-dimethylnaphtho[1,2-d]thiazol-1-ium methosulphate
3-ethyl-2,5,6-trimethylbenzoxazol-3-ium iodide
2-methyl-1-(3-sulphonatopropyl)naphtho[1,2-d]thiazol-1-ium
1-ethyl-2-methylnaphtho[1,2-d]thiazol-1-ium perchlorate
2-methyl-5-phenyl-3-(3-sulphonatopropyl)benzoxazol-3-ium
3-ethyl-6-methoxy-2-methylbenzothiazol-3-ium iodide
5-methoxy-1,2-dimethylnaphtho[1,2-d]thiazol-1-ium iodide
5-chloro-3-ethyl-2-methylbenzothiazol-3-ium toluene-4-sulphonate
5,6-dimethoxy-2,3-dimethylbenzothiazol-3-ium toluene-4-sulphonate
3-ethyl-2-methylbenzo[4,5]thieno[2,3-d]thiazol-3-ium toluene-4-sulphonate
3-ethyl-2-methylnaphtho[1,2-]thiazol-1-ium toluene-4-sulphonate
5,6-dichloro-3-ethyl-2-methyl-1-(3-sulphonatobutyl) 3H-benzoimidazol-1-ium
2,3-dimethyl-5-phenylbenzoxazol-3-ium methosulphate
5-methoxy-1,2-dimethylbenzo[cd]indolium perchlorate
1-butyl-2,3,3-trimethyl-3H-indolium iodide
1,1,2,3-tetramethyl-1H-benz[e]indolium iodide The compounds of formula (II) can be chosen from:

1,2-dimethylquinolinium iodide
1,2-dimethylquinolinium chloride
1,4-dimethylquinolinium iodide
1-ethyl-2-methylquinolinium tetrafluoroborate
2-methyl-1-(3-sulphonatopropyl)quinolinium
2,3-dimethylisoquinolinium iodide
4-chloro-1,2-dimethylquinolinium methosulphate
7-chloro-1,4-dimethylquinolinium
1-ethyl-2,6-dimethylquinolinium iodide
4-methoxy-1,2-dimethylquinolinium iodide
1-ethyl-4-methylquinolinium iodide
1,2,3,4-tetrahydropyrido[1,2-a]quinolinylium toluene-4-sulphonate
1,1'-trimethylenebis(2,4-dimethylpyridinium) bromide
1,1'-tetramethylenebis(2,5-dimethylpyridinium) perchlorate
1,1'-(oxydiethylene)bis(2-methylquinolinium) perchlorate
1,2-dimethylpyridinium methosulphate
1,2,4-trimethylpyridinium chloride
1,2,4,6-tetramethylpyridinium chloride
4-methoxy-1,2,6-trimethylpyridinium perchlorate
1-(2-hydroxyethyl)-3-methylpyridinium chloride The aldehyde corresponds to formula (III) below:

(III)

in which:

$R_6$ denotes a group of formula (III A) below:

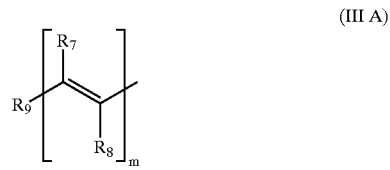

(III A)

in which:

$R_7$ and $R_8$, which may be identical or different, denote a hydrogen atom or an alkyl, mono- or polyhydroxyalkyl, alkylhydroxyalkyl, alkoxy, —$CF_3$, or —$OCF_3$ group, $R_7$ and $R_8$ can also form, together with the atoms to which they are attached, an aryl ring or a 5- or 6-membered heterocyclic ring, it being possible for the said rings to be substituted or unsubstituted;

m denotes an integer from 0 to 3, $R_8$ denotes the substituents denoted by $R_7$, a substituted or unsubstituted aryl or alkylaryl group or a substituted or unsubstituted 5- or 6-membered heterocyclic group, or to the cosmetically acceptable salts of these compounds.

The ketone can be chosen from the ketones of formula (IV) or (V) below:

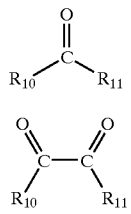

(IV)

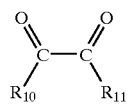

(V)

in which;

$R_{10}$ denotes the substituents denoted by $R_6$, $R_{11}$ denotes an alkyl, mono- or polyhydroxyalkyl or alkylhydroxyalkyl group, or a substituted or unsubstituted aryl, alkylaryl or 5- or 6-membered heterocyclic group, $R_{10}$ and $R_{11}$ can also form, together with the atoms to which they are attached, a 5- or 6-membered aryl ring or a heterocyclic ring comprising hetero atoms such as N or S, it being possible for the said ring itself to be attached to a 5- or 6-membered aryl ring or to a heterocycle comprising hetero atoms such as N or S, it being possible for the said rings to be substituted or unsubstituted, or to cosmetically acceptable salts of these compounds.

The quinone can correspond to formulae (VI) and (VII) below:

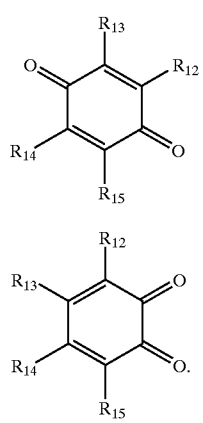

(VI)

(VII)

in which:

$R_{12}$ denotes a hydrogen or halogen atom or a sulphonic or alkoxy group, $R_{13}$, $R_{14}$ and $R_{15}$, which may be identical or different, denote a hydrogen or halogen atom, a hydroxyl, alkyl, mono- or polyhydroxyalkyl, alkylhydroxyalkyl, alkylsulphonyl, carboxyalkyl, aminoalkyl, alkylaminoalkyl, (dihydroxy)alkylaminoalkyl or alkyl-NR'R" group (with R' and R" denoting alkyl or possibly forming, together with the nitrogen atom to which they are attached, an aryl ring or a 5- or 6-membered heterocycle), an aryl group or an amino group which can be substituted with an alkyl or a hydroxyalkyl, $R_{12}$ and $R_{13}$, $R_{13}$ and $R_{14}$ or $R_{14}$ and $R_{15}$ can form, together with the atoms to which they are attached, a substituted or unsubstituted aryl ring or 5- or 6-membered heterocycle;

or to the cosmetically acceptable salts of these compounds.

The diiminoisoindoline or 3-aminoisoindolone derivatives can be those corresponding to formula (VIII) below:

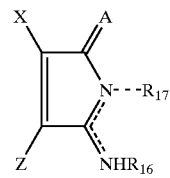

(VIII)

in which:

$R_{16}$ and $R_{17}$, which may be identical or different, denote a hydrogen atom, an alkyl, mono- or polyhydroxyalkyl, alkylhydroxyalkyl, aminoalkyl, alkylaminoalkyl or (dihydroxy)alkylaminoalkyl group or an alkyl-NR'R" group, with R' and R" denoting alkyl or possibly forming, together with the nitrogen atom to which they are attached, an aryl ring or a 5- or 6-membered heterocycle, A denotes an oxygen atom or NH, X and Z together form a substituted, or unsubstituted aryl ring or 5- or 6-membered heterocycle;

or to the cosmetically acceptable salts of these compounds.

Among the preferred compounds of formula (III) which may be mentioned in particular are benzaldehyde, 2,3,4-monohydroxybenzaldehydes, 2,3,4-monomethoxybenzaldehydes, 2,3,4-monomethylbenzaldehydes, (2,3)-, (2,4)-, (2,5)-, (2,6)- and (3,5)-dihydroxybenzaldehydes, (2,3)-, (2,4)-, (2,5)-, (2,6)- and (3,5)-dimethoxybenzaldehydes, vanillin, isovanillin, syringaldehyde (2,3)-, (2,4)-, (2,5)-, (2,6)- and (3,5)-dimethylbenzaldehydes, 4-isopropylbenzaldehyde, 4-dimethylaminobenzaldehyde, 4-diethylaminobenzaldehyde, piperonal, (2,6)- and (3,5)-dimethyl-4-hydroxybenzaldehyde, 2,3,4-mononitrobenzaldehydes, 2-hydroxy-3-methoxybenzaldehyde, 2-hydroxy-4-methoxybenzaldehyde, 2-hydroxy-5-methoxybenzaldehyde, 2-hydroxy-6-methoxybenzaldehyde, 4-methylthiobenzaldehyde, (2,3,4)-, (2,4,6)-, (3,4,5)-, (2,4,5)-trihydroxybenzaldehydes, methyl 2-, 3- and 4-formylbenzoates, 2,3,4-mono-(2-hydroxyethoxy) benzaldehydes, 4-nitro-3-hydroxybenzaldehyde, 3-nitro-4-hydroxybenzaldehyde, 2-nitro-4-hydroxybenzaldehyde, 3-nitro-2-hydroxybenzaldehyde, 2,3,4-monotrifluorobenzaldehydes, 2,3-dihydroxy-4-methoxybenzaldehyde, 3,4-dihydroxy-5-methoxybenzaldehyde, 3,5-dihydroxy-4-methoxybenzaldehyde, 3-methoxy-2-nitrobenzaldehyde, 4-methoxy-2-nitrobenzaldehyde, 2-methoxy-3-nitrobenzaldehyde, 4-methoxy-3-nitrobenzaldehyde, (2,3,4)-, (2,4,6)-, (3,4,5)- and (2,4,5)-trimethoxybenzaldehydes, 5-nitrovanillin, (2,4)- and (2,6)-dinitrobenzaldehydes, pentamethylbenzaldehyde, 4-methysulphonylbenzaldehyde, 2,3,4-monoformylphenoxyacetic acids, 4-diethylaminosalicylaldehyde, 4-(3-dimethylaminopropoxy)benzaldehyde, 2,3-dihydrobenzo(b)furan-5-carboxaldehyde, 1- and 2-naphthaldehyde, 6- and 5-carboxaldehyde-1,4-benzodioxane, 2,4-monohydroxy-1-naphthaldehydes, 1-monohydroxy-2-naphthaldehyde, 1-(4- formylphenyl)imidazole, 4-pyrrolidinolbenzaldehyde, 2,4-monomethoxy-1-naphthaldehydes, 2,3-dimethylchroman-6-carboxaldehyde, 2,3,6,7-tetrahydro-1H,5H-pyrido(3,2,1-IJ) quinoline-9-carbaldehyde, 4-dimethylamino-1-naphthaldehyde, 9-anthraldehyde, 3-nitro-4-pyrrolidinobenzaldehyde, 3-nitro-4-piperidinobenzaldehyde, 3-nitro-4-morpholinobenzaldehyde, pyridine 2,3,4-monocarboxaldehydes, 5-formyl-6-methyluracil, pyridoxal, quinoline-2,3,4-monocarboxaldehydes, 8-hydroxyquinoline-2-carboxaldehyde, 2- and 3-furaldehydes, 2- and 3-thienylcarboxaldehydes, 2- and 3-imidazocarboxaldehydes, 2-pyrrolecarboxaldehyde, 5-nitro-2-furaldehyde, 5-(dimethylamino)-2-furaldehyde, pyrozole-3-carbaldehyde, 5-nitro-2-thiophenecarboxaldehyde, 5-nitro-3-thiophenecarboxaldehyde, indole-3-carboxaldehyde, N-methylindole-3-carboxaldehyde, 2-methylindole-3-carboxaldehyde, 4,5,6,7-monomethylindolecarboxaldehydes and 5-formyl-2-furansulphonic acid.

The ketones of formulae (IV) and (V) can be chosen from 2,3-indolinedione, 2,3-butanedione, 2,3-pentanedione, (2,3)- and (3,4)-hexanedione, 1-phenyl-1,2-propanedione, benzil, furil, 2,2'-pyridil, nitrobenzil, anisil, 3,3'-dimethoxybenzil, 4,4'-bis(dimethylamino)benzil, camphoroquinone, cyclohexane-1,2-dione, isatin, N-methylisatin, 4-, 5-, 6- and 7-monomethylisatin, (4,5)-, (4,7)-, (5,7)- and (6,7)-dimethylisatin, N-ethylisatin, N-hydroxymethylisatin, 5-, 6- and 7-monomethoxyisatin, 4-, 5-, 6- and 7-monochloroisatin, 4-, 5-, 6- and 7-monobromoisatin, N-isopropylisatin, N-butylisatin, N-propylisatin, 5-nitroisatin, isatin-5-sulphonic acid, 2,4,5-trihydroxypyrimidine, alloxan, 1,3-dimethylhexahydro-2,4, 5,6-pyrimidinetetrone, ninhydrin, chinisatin, 1,3-indenedione, squaric acid, croconic acid, 3,4-dimethoxy-3-cyclobutene-1,2-dione, 3- and 4-ethoxy-3-cyclobutene-1,2-dione, 3- and 4-isopropoxy-3-cyclobutene-1,2-dione, 3,4-di-N-butoxy-3-cyclobutene-1,2-dione, rhodizonic acid, oxindole, N-methyl-2-indolinone, N-methylnitro-2-indolinone, 6-methoxyoxindole, 5,6-dimethoxyoxindole and 5- and 6- monochlorooxindole.

The preferred quinones of formulae (VI) and (VII) are, inter alia, 1,4-naphthoquinone, spinulosin, atromentin, aurentioglycoladin, 2,5-dihydroxy-6-methylbenzoquinone, 2-hydroxy-3-methyl-6-methoxylbenzoquinone, 2,5-dihydroxy-3,6-diphenylbenzoquinone, 2,3-dimethyl-5-hydroxy-6-methoxybenzoquinone, 2,5-dihydroxy-6-isopropylbenzoquinone, lawsone, juglone, fafioline, naphthazarine, naphthopurpurine, lapachol, plumbagin, chloroplumbagin, droserone, shikonine, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphtoquinone, 3-methoxy 5-hydroxy-1,4-naphthoquinone, (1,4) and (1,2)-naphthoquinone, 4,5-dimethoxy-1,2-benzoquinone, phenanthrenequinone and (1,2)-naphthoquinone-4-sulphonic acid.

The derivatives of formula (VIII) are represented in particular by 3-imino-3H-isoindolylamine, 3-imino-4-methyl-3H-isoindol-1-ylamine, 3-imino-4-tert-butyl-3H-isoindol-1-ylamine, 3-imino-7-nitro-3H-isoindol-1-ylamine, 3-amino-1-imino-1H-isoindol-4-ol, 3-imino-7-isopropoxy-3H-isoindol-1-ylamine, 3-imino-7-(2,2,2-trifluoroethoxy)-3H-isoindol-1-ylamine, 3-imino-7-ethoxy-3H-isoindol-1-ylamine, 3-imino-7-butoxy-3H-isoindol-1-ylamine, 3-amino-1-imino-1H-isoindol-4-sulphonic acid, 3-imino-7-chloro-3H-isoindol-1-ylamine, 3-imino-5-methyl-3H-isoindol-1-ylamine, 3-imino-5-ethyl-3H-isoindol-1-ylamine, 3-imino-5-tert-butyl-3H-isoindol-1-ylamine, 3-imino-5-amino-3H-isoindol-1-ylamine, N-(1-amino-3-imino-3H-isoindol-5-yl)-acetamide, 3-imino-5-nitro-3H-isoindol-1-ylamine, 3-imino-5-fluoro-3H-isoindol-1-ylamine, 3-imino-5-chloro-3H-isoindol-1-ylamine, 3-imino-5-methylsulphanyl-3H-isoindol-1-ylamine, 3-imino-5-methoxy-3H-isoindol-1-ylamine, 3-imino-5-ethoxy-3H-isoindol-1-ylamine, 3-imino-5-propoxy-3H-isoindol-1-ylamine, 3-imino-5-isopropoxy-3H-isoindol-1-ylamine, 3-imino-5-butoxy-3H-isoindol-1-ylamine, 3-imino-5-isobutoxy-3H-isoindol-1-ylamine, 3-imino-5-tert-butoxy-3H-isoindol-1-ylamine, 3-imino-5-(2,2,2-trifluoromethyl)-3H-isoindol-1-ylamine, 3-imino-5-(2,2,2-trifluoroethoxy)-3H-isoindol-1-ylamine, 3-imino-5-methanesulphonyl-3H-isoinidol-1-ylamine, 3-imino-5,6-dimethyl-3H-isoindol-1-ylamine, 3-imino-5,6-diethyl-3H-isoindol-1-ylamine, 3-imino-5,6-dimethoxy-3H-isoindol-1-ylamine, 3-imino-5,6-diethoxy-3H-isoindol-1-ylamine, 3-imino-5,6-dibutoxy-3H-isoindol-1-ylamine, 3-imino-5,6-bis(trifluoromethyl)-3H-isoindol-1-ylamine, 3-imino-5,6-dichloro-3H-isoindol-1-ylamine, 5,6-bis(ethoxymethyl)3-imino-3H-isoindol-1-ylamine, 3-amino-1-imino-1H-isoindol-4,7-diol, 4,7-dichloro-3-imino-3H-iosindol-1-ylamine, 4,5,7-trichloro-3-imino-N6,N6-dimethyl-3H-isoindol-1,6-diamine, 4,5,6,7-tetrachloro-3-imino-3H-isoindol-1-ylamine, 4,5,6,7-tetrafluoro-3-imino-3H-isoindol-1-ylamine, 3-butylimino-3H-isoindol-1-ylamine, 2-(3-aminoisoindol-1-ylideneamino)ethanol, 3-(3-aminoisoindol-1-ylideneamino)-3-methylpentane-1,5-diol, N-(3-aminoisoindol-1-ylidene)guanidine, 7-imino-7H-pyrrolo[3,4-b]pyrid-5-ylamine, 7-imino-7H-pyrrolo-[3,4-b] pyrazin-5-ylamine, 7-imino-2,3-dimethyl-7H-pyrrolo[3,4-b]pyrazin-5-ylamine, 7-imino-7H-[1,4]dithiino[2,3-c] pyrrol-5-ylamine, 7-imino-2,3-dimethyl-7H-[1,4]dithiino[2, 3-c]pyrrol-5-ylamine, 7-imino-2,3-dihydro-7H-[1,4]dithiino [2,3-c]pyrrol-5-ylamine, 7-imino-2-methyl-2,3-dihydro-7H-[1,4]dithiino[2,3-c]pyrrol-5-ylamine, 3-aminoisoindol-1-one, 3-amino-7-methylisoindol-1-one, 3-amino-7-hydroxymethylisoindol-1-one, 3-amino-7-chloroisoindol-1-one, 3-amino-4-chloroisoindol-1-one, 3-amino-1-oxo-1H-isoindol-4-sulphonic acid, 3-amino-4-nitroisoindol-1-one, 3-amino-6-nitroisoindol-1-one, 3-amino-6-methylisoindol-1-one, 3-amino-6-chlorbisoindol-1-one, 3-amino-6-bromoisoindol-1-one, 3-amino-6-methylsulphanylisoindol-1-one, 3-amino-6-methoxyisoindol-1-one, 3-amino-5-chloroisoindol-1-one, 3-amino-5-fluoroisoindol-1-one, 3-amino-5-methoxyisoindol-1-one, 3-amino-5-nitroisoindol-1-one, ethyl 3-amino-1-oxo-1H-isoindole-5-carboxylate, 3-amino-5,6-dichloroisoindol-1-one, 3-amino-5,6-dibromoisoindol-1-one, 3-amino-4,7-dichloroisoindol-1-one, 3-amino-4,5,7-trichloroisoindol-1-one, 3-amino-4,5, 6,7-tetrachloroisoindol-1-one, 3-amino-4,5,7-trichloro-6-methylsulphanylisoindol-1-one, 3-amino-4,5,6,7-tetrabromoisoindol-1-one, 3-amino-4,5,6,7-tetrafluoroisoindol-1-one, 3-methylaminoisoindol-1-one, 3-ethylaminoisoindol-1-one, 3-propylaminoisoindol-1-one, 3-dimethylaminoisoindol-1-one, 7-ethylaminopyrrolo[3,4-b]pyrid-5-one, 7-aminopyrrolo[3,4-b]pyrid-5-one, 3-aminopyrrolo-[3,4-c]pyrid-5-one, 3-amino-6-methylpyrrolo[3,4-c]-pyrid-1-one, 5-aminopyrrolo[3,4-b]pyrid-7-one, 7-amino-pyrrolo[3,4-b]pyrazin-5-one, 1-amino-2-methylpyrrolo-[3,4-b]pyrazin-5-one, 7-amino-2,3-dimethylpyrrolo-[3,4-b]pyrazin-5-one, 7-amino-2,3-dihydro[1,4]dithiino-[2,3-c]pyrrol-5-one, 3-imino-2-methyl-2,3-dihydroisoindol-1-one, 3-imino-2-ethyl-2,3-dihydroisoindol-1-one, 3-imino-2-propyl-2,3- dihydroisoindol-1-one, 2-hydroxymethyl-3-imino-2,3-dihydroisoindol-1-one, 2-(2-hydroxyethyl)-3-imino-2,3-dihydroisoindol-1-one, 2-(1-imino-3-oxo-1,3-dihydroisoindol-2-yl)ethane sulphonic acid, 3-(1-imino-3-oxo-1,3-dihydroisoindol-2-yl)propionic acid, 2-(3-hydroxypropyl)-3-imino-2,3-dihydroisoindol-1-one and 5-imino-6-methyl-5,6-dihydropyrrolo[3,4-b]pyridin-7-one.

In the context of the present invention:

The halogen atoms preferentially denote a fluorine, chlorine, bromine or iodine atom.

The alkyl, monohydroxyalkyl, polyhydroxyalkyl, alkylhydroxyalkyl, alkylsulphonyl, carboxyalkyl, aminoalkyl, alkylaminoalkyl and dihydroxyaminoalkyl radicals can be linear or branched.

The alkyl groups in particular denote groups of 1 to 20 carbon atoms such as, for example, methyl, ethyl, propyl, isopropyl, n-propyl, butyl, n-butyl, tert-butyl, pentyl, n-pentyl, isopentyl, n-hexyl, iso-hexyl, heptyl, octyl, nonyl, decyl, undecyl, dodecyl and pentadecyl groups. The alkyl groups preferably denote a group of 1 to 6 carbon atoms; these alkyl groups can be substituted; for example, with a halogen atom or a cyano or hydroxyl radical, and can thus represent trifluoromethyl, δ-chloropropyl, β-cyanoethyl or β-hydroxyethyl radicals.

Among the monohydroxyalkyl groups which may be mentioned in particular are hydroxymethyl, hydroxyethyl, hydroxypropyl and hydroxybutyl groups.

Among the polyhydroxyalkyl radicals which may be mentioned in particular are dihydroxyethyl, dihydroxypropyl, trihydroxypropyl and dihydroxybutyl radicals.

The alkoxy groups denote a group —O—R, R representing an alkyl group as defined above.

The alkenyl groups denote a monovalent radical corresponding to the ethylenic carbons, such as, for example, alkyl or 3,3-dimethylallyl.

The acetyloxy groups denote a group —O—CO—R, R representing an alkyl group as defined above.

Among the cycloalkyl radicals which may be mentioned in particular are cyclohexyl and cyclopentyl.

Among the aryl radicals which may be mono- or polycyclic, mention may be made in particular of phenyl and naphthyl groups.

Among the heterocycles, which may be mono- or polycyclic and containing one or more hetero atoms, mention may be made of thiophene, pyrrole, imidazole, pyrazole, triazole, thiazole, furan, benzofuran, benzimidazole, benzothiazole, pyridyl, benzoxazole, quinolyl, quinazolyl, quinoxalyl and naphthyl rings.

Among the alkylaryl radicals which may be mentioned in particular are benzyl, phenethyl and naphthylmethyl groups.

The aminoaryl groups denote groups —NHR, R representing an aryl radical.

In the context of the present invention, the cycloalkyl and aryl radicals and the heterocycles can be substituted or polysubstituted, for example with a halogen, with a $C_1$–$C_4$ alkyl, a $C_1$–$C_4$ alkoxy, a nitro group, a hydroxyl group, a carboxylic group, a $C_1$–$C_4$ acetyloxy group, a carboxamide group, a sulphonamide, sulphonic, nitrile, —$CF_3$ or —$OCF_3$ group or with a cycloalkyl or aryl radical which may be substituted with a $C_1$–$C_4$ alkyl.

In the context of the present invention, the formulae (I) to (VIII) are not limited to those specifically described, but also comprise the tautomeric forms thereof, when they exist.

For the purposes of the present invention, the cosmetically acceptable salts of the abovementioned compounds can be hydrochlorides, oulphates, hydrobromides or tartrates.

The compositions for dyeing keratin fibres, in particular human keratin fibres such as the hair, in accordance with the present invention are essentially characterized in that they comprise at least one cationic derivative as defined above and at least one compound chosen from an aldehyde as defined above, a ketone as defined above, a quinone and a diiminoisoindoline or 3-aminoisoindolone derivative as defined above, in a medium which is suitable for dyeing.

The cationic derivative of these compositions is preferably chosen from 3-ethylmethylbenzothiazolium iodide, 1,2,3,3-tetramethyl-3H-indolium iodide, 3-ethylmethylbenzoxazolium iodide, 1,2-dimethylquinolinium iodide, 5-chloro-3-ethyl-2-methylbenzothiazolium iodide and 2-methyl-1-(3-sulphopropyl)naphtho[1,2-d]-thiazolium betaine.

In one preferred embodiment of the invention, the compound chosen from an aldehyde of formula (III), a ketone of formula (IV) or (V), a quinone and a diiminoisoindoline or 3-aminoisoindolone derivative is chosen from 1,4-naphthoquinone, isatin, N-methylisatin, 3-imino-3H-isoindol-1-ylamine, 4-dimethylaminobenzaldehyde and 4-dimethylaminonaphthaldehyde.

The cationic derivative can be present in a concentration ranging from 0.01% to 10%, and preferably between 0.05% and 5%, by weight relative to the total weight of the composition.

The compound chosen from an aldehyde of formula (III), a ketone of formula (IV) or (V), a quinone and a diiminoisoindoline or 3-aminoisoindolone derivative can be present in a concentration ranging from 0.01% to 10% and preferably from 0.05% to 5% by weight relative to the total weight of the composition.

The medium which is suitable for dyeing is preferably an aqueous medium consisting of water and/or of cosmetically acceptable organic solvents, and more particularly alcohols such as ethyl alcohol, isopropyl alcohol, benzyl alcohol and phenothyl alcohol, or glycols or glycol ethers such as, for example, ethylene glycol and its monomethyl, monoethyl arid monobutyl ethers, propylene glycol or its ethers such as, for example, propylene glycol monomethyl ether, butylene glycol, dipropylene glycol and diethylene glycol alkyl ethers such as, far example, diethylene glycol monoethyl ether or monobutyl ether, in concentrations of between about 0.5% and 20%, and preferably between about 2% and 10%, by weight relative to the total weight of the composition.

Fatty amides such as mono- and diethanolamides of acids derived from copra, of lauric acid or of oleic acid can also be added to the composition according to the invention, in concentrations of between about 0.05% and 10% by weight.

Surfactants that are well known in the prior art and of anionic, cationic, nonionic, amphoteric or zwitterionic type or mixtures thereof can also be added to the composition according to the invention, preferably in a proportion of between about 0.1% and 50% by weight and advantageously between about 1% and 20% by weight relative to the total weight of the composition.

Thickeners can also be used in a proportion ranging from about 0.2% to 20%.

The said dye composition can also contain various common adjuvants such as antioxidants, fragrances, sequestering agents, dispersants, hair conditioners, preserving agents and opacifiers, as well as any other additive usually used in the dyeing of keratin substances.

Needless to say, a person skilled in the art will take care to select the optional additional compound(s) mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 2 to 11 and preferably from 5 to 10, and it being possible for it to be adjusted by means of basifying or acidifying agents or buffers that are previously well known.

Basifying agents which may be mentioned are aqueous ammonia, alkaline carbonates, alkanolamines, for example mono-, di- and triethanolamine and derivatives thereof, sodium hydroxide, potassium hydroxide and the compounds of formula:

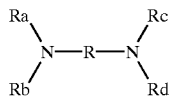

in which R is a propylene residue optionally substituted with a hydroxyl group or a $C_1$–$C_4$ alkyl radical; Ra, Rb, Rc and Rd, simultaneously or independently of each other, represent a hydrogen atom or a $C_1$–$C_4$ alkyl or $C_1$–$C_4$ hydroxyalkyl radical.

The acidifying agents are conventionally mineral or organic acids such as, for example, hydrochloric acid, tartaric acid, citric acid and phosphoric acid.

Among the buffers which may be mentioned, for example, is potassium dihydrogen phosphate/sodium hydroxide.

The composition applied to the hair can be in various forms, such as in the form of a liquid, cream or gel or in any other form which is suitable for dyeing keratin fibres. In particular, it can be packaged under pressure in an aerosol can in the presence of a propellant and can form mousse.

In accordance with the present invention, the process for dyeing keratin fibres, in particular human keratin fibres such as the hair, is essentially characterized in that a component (A) consisting of a composition containing, in a medium which is suitable for dyeing, at least one cationic derivative as defined above, and a component (B) consisting of a composition containing, in a medium which is suitable for dyeing, at least one compound chosen from an aldehyde of formula (III), a ketone of formula (IV) or (V), a quinone and a diiminoisoindoline or 3-aminoisoindolone derivative such as, for example, one of those defined above, is applied to the said fibres so as to allow the development of a coloration on the said keratin fibres.

In one preferred embodiment of the process of the invention, the components (A) and (B) are mixed together just before use, and the resulting composition is then applied immediately to the keratin fibres, and is left to act on them for 1 to 60 minutes and preferably from 1 to 30 minutes. The keratin fibres are then rinsed, washed with shampoo, rinsed again and then dried.

Another process of the present invention consists essentially in applying component (A) to the keratin fibres, followed or preceded by application of component (B) to the said fibres, in leaving each component to act for 1 to 60 minutes and preferably from 1 to 30 minutes, and in optionally rinsing with water between each application; the keratin fibres are then rinsed, washed with shampoo, rinsed again and then dried.

A subject of the invention is also an agent for dyeing keratin fibres, in particular human hair, characterized in that it consists of components (A) and (B) stored separately, as defined above.

Components (A) and (B) are intended either to be mixed together immediately before use or to be applied successively to the fibres to be treated.

According to one embodiment, the various components (A) and (B) can be packaged in a multi-compartment device also known as a "dyeing kit" comprising all the components intended to be applied for the same dyeing operation on keratin fibres, in particular human keratin fibres such as the hair, in successive applications with or without premixing.

Such devices can comprise a first compartment containing component (A) containing the cationic derivative and a second compartment containing component (B) containing the compound chosen from an aldehyde, a ketone, a quinone and a diiminoisoindoline or 3-aminoisoindolone derivative.

Another variant can also consist in storing component (A) or component (B) in an anhydrous solvent medium and in providing a third compartment containing a cosmetically acceptable aqueous medium which is suitable for dyeing. In this case, the contents of the third compartment are mixed, immediately before use, into one or other of the two compartments containing the anhydrous components (A) and (B), or alternatively the three compartments are mixed together before use.

Concrete examples illustrating the invention will now be given.

EXAMPLE 1

The dye composition below was prepared just before use:

| | |
|---|---|
| 3-imino-3H-isoindol-1-ylamine | 0.435 g |
| 3-ethylmethylbenzothiazolium iodide | 0.915 g |
| ethyl alcohol | 30.0 |
| water | qs 100 g |

The above composition was applied to locks of natural grey hair containing 90% white hairs, and was left to stand on the hair for 30 minutes. After rinsing with running water and drying, the hair was dyed in a golden yellow shade.

EXAMPLE 2

The dye composition below was prepared just before use:

| | |
|---|---|
| 4-dimethylaminobenzaldehyde | 0.447 g |
| 3-ethyltmethylbenzothiazolium iodide | 0.915 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was dyed in a bright pink shade.

EXAMPLE 3

The dye composition below was prepared just before use:

| | |
|---|---|
| 1,4-naphthoquinone | 0.474 g |
| 3-ethylmethylbenzothiazolium iodide | 0.915 g |
| ethyl alcohol | 30.0 g |
| water | qs 100 g |

The above composition was applied to locks of permanent-waved grey hair containing 90 white hairs, and was left to stand on the hair for 30 minutes. After rinsing with running water and drying, the hair was dyed in a blue-violet shade.

EXAMPLE 4

The dye composition below was prepared just before use:

| | |
|---|---|
| 1,4-naphthoquinone | 0.474 g |
| 1,2,3,3-tetramethyl-3H-indolium iodide | 0.903 g |
| ethyl alcohol | 30.0 g |
| water | qs 100 g |

The above composition was applied to locks of bleached hair, and was lets to stand on the hair for 30 minutes. After rinsing with running water and drying, the hair was dyed in a violet shade.

EXAMPLE 5

The dye composition below was prepared just before use:

| | |
|---|---|
| isatin | 0.441 g |
| 1,2,3,3-tetramethyl-3H-indolium iodide | 0.915 g |
| ethyl alcohol | 30.0 g |
| water | qs 100 g |

The above composition was applied to locks of bleached hair, and was left to stand on the hair for 30 minutes. After rinsing with running water and drying, the hair was dyed in a light orange shade.

EXAMPLE 6

The dye composition below was prepared just before use:

| | |
|---|---|
| 4-dimethylaminobenzaldehyde | 0.447 g |
| 1,2,3,3-tetramethyl-3H-indolium iodide | 0.915 g |
| ethyl alcohol | 30.0 g |
| water | qs 100 g |

The above composition was applied to locks of permanent-waved grey hair, and was left to stand on the hair for 30 minutes. After rinsing with running water and drying, the hair was dyed in a raspberry-red shade.

EXAMPLE 7

The dye composition below was prepared just before use:

| | |
|---|---|
| 3-imino-3H-isoindol-1-ylamine | 0.435 g |
| 1,2,3,3-tetramethyl-3H-indolium iodide | 0.903 g |
| ethyl alcohol | 30.0 g |
| water | qs 100 g |

The above composition was applied to locks of bleached hair, and was left to stand on the hair for 30 minutes. After rinsing with running water and drying, the hair was dyed in a pale apricot shade.

EXAMPLE 8

The dye composition below was prepared just before use:

| | |
|---|---|
| 1,4-naphthoquinone | 0.474 g |
| 3-ethylmethylbenzoxazolium iodide | 0.867 g |
| ethyl alcohol | 30.0 g |
| water | qs 100 g |

The above composition was applied to locks of bleached hair, and was left to stand on the hair for 30 minutes. After rinsing with running water and drying, the hair was dyed in a pale coppery shade.

EXAMPLE 9

The dye composition below was prepared just before use:

| | |
|---|---|
| 1,4-naphthoquinone | 0.474 g |
| 3-ethylmethylbenzoxazolium iodide | 0.867 g |
| ethyl alcohol | 30.0 g |
| water | qs 100 g |

The above composition was applied to locks of bleached hair, and was left to stand on the hair for 30 minutes, After rinsing with running water and drying, the hair was dyed in a pale coppery shade.

EXAMPLE 10

The dye composition below was prepared just before use:

| | |
|---|---|
| isatin | 0.441 g |
| 3-ethylmethylbenzoxazolium iodide | 0.867 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was dyed in a sandy shade.

EXAMPLE 11

The dye composition below was prepared just before use:

| | |
|---|---|
| 4-dimethylaminobenzaldehyde | 0.447 g |
| 3-ethylmethylbenzoxazolium iodide | 0.867 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was dyed in a pale straw shade.

EXAMPLE 12

The dye composition below was prepared just before use:

| | |
|---|---|
| 3-imino-3K-isoindol-1-ylamine | 0.435 g |
| 3-ethylmethylbenzoxazolium iodide | 0.867 g |
| ethyl alchohol | 30.0 g |
| water | qs |
| | 100 g |

The above composition was applied to locks of bleached grey hair, and was left to stand on the hair for 30 minutes. After rinsing with running water and drying, the hair was dyed in a pale straw shade.

EXAMPLE 13

The dye composition below was prepared just before use:

| | |
|---|---|
| 3-imino-3H-isoindol-1-ylamine | 0.435 g |
| 1,2-dimethylquinolinium iodide | 0.805 g |
| ethyl alcohol | 300 g |
| water | qs |
| | 100 g |

The above composition was applied to locks of bleached hair, and was left to stand on the hair for 30 minutes. After rinsing with running water and drying, the hair was dyed in a straw-yellow shade.

EXAMPLE 14

The dye composition below was prepared just before use:

| | |
|---|---|
| 4-dimethylaminobenzaldehyde | 0.447 g |
| 1,2-diethylquinolinium iodide | 0.805 g |
| ethyl alcohol | 30.0 g |
| water | qs |
| | 100 g |

The above composition was applied to locks of permanent-waved grey hair containing 90% white hairs, and was left to stand on the hair for 30 minutes. After rinsing with running water and drying, the hair was dyed in a pink-orange shade.

EXAMPLE 15

The dye composition below was prepared just before use:

| | |
|---|---|
| 1,4-naphthoquinone | 0.474 g |
| 1,2-dimethylquinolinium iodide | 0.805 g |
| ethyl alcohol | 30.0 g |
| water | qs |
| | 100 g |

The above composition was applied to locks of natural grey hair containing 90% white hairs, and was left to stand on the hair for 30 minutes. After rinsing with running water and drying, the hair was dyed in a yellow-green shade.

EXAMPLE 16

The dye composition below was prepared just before use:

| | |
|---|---|
| isatin | 0.441 g |
| 1,2-dimethylquinolinim iodide | 0.805 g |
| ethyl alcohol | 30.0 g |
| water | qs |
| | 100 g |

The above composition was applied to locks of beached hair, and was left to stand on the hair for 30 minutes. After rinsing with running water and drying, the hair wan dyed in a golden yellow shade.

EXAMPLE 17

The dye composition below was prepared just before use:

| | |
|---|---|
| 4-dimethylaminobenzaldehyde | 0.447 g |
| 5-chloro-3-ethyl-2-methylbenzothiazolium iodide | 1.151 g |
| ethyl alcohol | 30.0 g |
| water | qs |
| | 100 g |

The above composition was applied to locks of beached hair, and was left to stand on the hair for 30 minutes. After rinsing with running water and drying, the hair was dyed in a violet-red shade.

EXAMPLE 18

The dye composition below was prepared just before use:

| | |
|---|---|
| 3-imino-3H-isoindol-1-ylamine | 0.435 g |
| 5-chloro-3-ethyl-2-methylbenzothiazolium toluene-4-sulphonate | 1.151 g |
| ethyl alcohol | 30.0 g |
| water | qs |
| | 100 g |

The above composition was applied to locks of beached hair, and was left to stand on the hair for 30 minutes. After rinsing with running water and drying, the hair was dyed in a lemon yellow shade.

EXAMPLE 19

The dye composition below was prepared just before use:

| | |
|---|---|
| 1,4-naphthoquinone | 0.474 g |
| 5-chloro-3-ethyl-2-methylbenzothiazolium toluene-4-sulphonate | 1.151 g |
| ethyl alcohol | 30.0 g |
| water | qs |
| | 100 g |

The above composition was applied to locks of beached hair, and was left to stand on the hair for 30 minutes. After rinsing with running water and drying, the hair was dyed in a blue-violet shade.

EXAMPLE 20

The dye composition below was prepared just before use:

| | |
|---|---|
| isatin | 0.441 g |
| 5-chloro-3-ethyl-2-methylbenzo-thiazolium toluene-4-sulphonate | 1.151 g |
| ethyl alcohol | 30.0 g |
| water | qs 100 g |

The above composition was applied to locks of beached hair, and was left to stand on the hair for 30 minutes. After rinsing with running water and drying, the hair was dyed in a golden yellow shade.

EXAMPLE 21

The dye composition below was prepared just before use:

| | |
|---|---|
| 4-dimethylaminobenzaldehyde | 0.447 g |
| 2-methyl-1-(3-sulphopropyl)naphtho[1,2-d] thiazolium betaine | 0.963 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a light rosewood shade.

EXAMPLE 22

The dye composition below was prepared just before use:

| | |
|---|---|
| 3-imino-3H-isoindol-1-ylamine | 0.435 g |
| 2-methyl-1-(3-sulphopropyl)naphtho[1,2-d] thiazolium betaine | 0.963 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a light orange shade.

EXAMPLE 23

The dye composition below was prepared just before use:

| | |
|---|---|
| 1,4-naphthoquinone | 0.474 g |
| 2-methyl-1-(3-sulphopropyl)naphtho[1,2-d] thiazolium betaine | 0.963 g |
| benzyl alcohol | 7.0 g |
| ethyl alcohol | 23.0 g |
| water | qs 100 g |

The above composition was applied to locks of natural grey hair containing 90% white hairs, and was left to stand on the hair for 30 minutes. After rinsing with running water and drying, the hair was dyed in a green shade.

EXAMPLE 24

The dye composition below was prepared just before use:

| | |
|---|---|
| isatin | 0.441 g |
| 2-methyl-1-(3-sulphopropyl)naphtho[1,2-d] thiazolium betaine | 0.963 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a light orange shade.

EXAMPLE 25

The dye composition below was prepared just before use:

| | |
|---|---|
| 4-dimethylaminobenzaldehyde | 0.447 g |
| 5-methoxy-2-methyl-3-(3-sulphopropyl)-benzothiazolium betaine | 0.904 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a rosewood shade.

EXAMPLE 26

The dye composition below was prepared just before use:

| | |
|---|---|
| 3-imino-3H-isoindol-1-ylamine | 0.435 g |
| 5-methoxy-2-methyl-3-(3-sulphopropyl)-benzothiazolium betaine | 0.904 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a golden yellow shade.

EXAMPLE 27

The dye composition below was prepared just before use:

| | |
|---|---|
| 1,4-naphthoquinone | 0.474 g |
| 5-methoxy-2-methyl-3-(3-sulphopropyl)- | 0.904 g |

-continued

| | |
|---|---|
| benzothiazolium betaine | |
| benzyl alcohol | 7.0 g |
| ethyl alcohol | 23.0 g |
| water | qs 100 g |

The above composition was applied to locks of natural grey hair containing 90% white hairs, and was left to stand on the hair for 30 minutes. After rinsing with running water and drying, the hair was dyed in a yellow-green shade.

EXAMPLE 28

The dye composition below was prepared just before use:

| | |
|---|---|
| isatin | 0.441 g |
| 5-methoxy-2-methyl-3-(3-sulphopropyl)-benzothiazolium betaine | 0.904 g |
| benzyl alcohol | 7.0 g |
| ethyl alcohol | 23.0 g |
| water | qs 100 g |

The above composition was applied to locks of permanent-waved grey hair containing 90% white hairs, and was left to stand on the hair for 30 minutes. After rinsing with running water and drying, the hair was dyed in a iridescent orange shade.

What is claimed is:

1. A process for dyeing at least one keratin fiber, comprising applying to said at least one keratin fiber a composition comprising:
    (a) at least one cationic compound chosen from:
        (1) compounds having formula (I) and the cosmetically acceptable salts thereof:

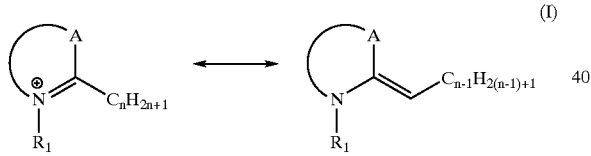

(I)

in which:
n is an integer ranging from 1 to 4;
$R_1$ is chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy) alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;
A and the nitrogen atom, N, together form at least one hydrocarbon-based ring, optionally substituted, chosen from unsaturated rings comprising 5 atoms; unsaturated rings comprising 6 atoms; aromatic rings comprising 5 atoms; and aromatic rings comprising 6 atoms;

wherein said at least one hydrocarbon-based ring may be interrupted by at least one atom chosen from nitrogen, oxygen and sulfur; it being possible for said at least one hydrocarbon-based ring to be fused with at least one ring chosen from unsubstituted aromatic rings and substituted aromatic rings; and A is chosen from carbon, optionally substituted; nitrogen, optionally substituted; oxygen; and sulfur; and (2) compounds having formula (II) and the cosmetically acceptable salts thereof:

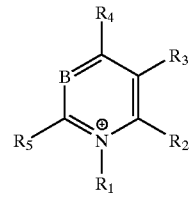

(II)

wherein:
$R_1$, $R_2$, $R_3$, $R_4$, and $R_5$, which may be identical or different, are each chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy)alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;

B is chosen from —CH— groups and nitrogen;
at least one of $R_1$ and $R_2$, $R_2$ and $R_3$, $R_3$ and $R_4$, $R_5$ and $R_1$, $R_5$ and B, and $R_4$ and B may also form, together with the atoms to which they are attached, at least one hydrocarbon-based ring, optionally substituted, chosen from 5-membered unsaturated rings; 6-membered unsaturated rings; 5-membered aryl rings; 6-membered aryl rings; 5-membered heterocycles; and 6-membered heterocycles; wherein said at least one hydrocarbon-based ring may be interrupted by at least one atom chosen from nitrogen and sulfur; and (b) at least one compound chosen from:
    (1) aldehydes having formula (III) and the cosmetically acceptable salts thereof:

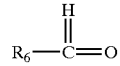

(III)

in which:

$R_6$ is chosen from groups having formula (III A):

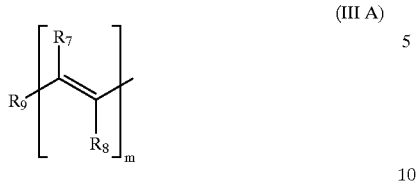

(III A)

in which:

$R_7$ and $R_8$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_7$ and $R_8$, which may be identical or different, may also form, together with the atoms to which they are attached, at least one ring, optionally substituted, chosen from aryl rings; 5-membered heterocyclic rings; and 6-membered heterocyclic rings;

m is an integer ranging from 0 to 3; and $R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;

(2) ketones chosen from ketones having formula (IV), ketones having formula (V), and the cosmetically acceptable salts thereof:

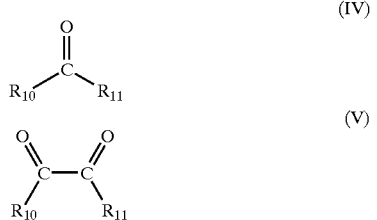

(IV)

(V)

in which:

$R_{10}$ is chosen from groups having formula (III A):

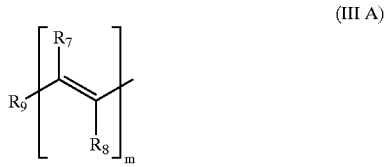

(III A)

in which:

$R_7$ and $R_8$, which may be identical or different, are each chosen from hydrogen; alkyl groups; monohydroxyalkyl groups; polyhydroxyalkyl groups; alkylhydroxyalkyl groups; alkoxy groups;

—$CF_3$ groups; and —$OCF_3$ groups;

$R_7$ and $R_8$, which may be identical or different, may also form, together with the atoms to which they are attached, at least one ring, optionally substituted, chosen from aryl rings; 5-membered heterocyclic rings; and 6-membered heterocyclic rings;

m is an integer ranging from 0 to 3;

$R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;

$R_{11}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered hetero-cyclic groups, optionally substituted; and 6-membered heterocyclic groups, optionally substituted; and $R_{10}$ and $R_{11}$ may also form, together with the atoms to which they are attached, at least one ring, optionally substituted, chosen from 5-membered aryl rings; 6-membered aryl rings; and heterocyclic rings; it being possible for said at least one ring itself to be attached to at least one additional ring, optionally substituted, chosen from 5-membered aryl rings, 6-membered aryl rings and heterocyclic rings comprising at least one heteroatom;

(3) quinones and the cosmetically acceptable salts thereof;

(4) diiminoisoindoline derivatives and the cosmetically acceptable salts thereof; and (5) 3-aminoisoindolone derivatives and the cosmetically acceptable salts thereof;

it with the proviso that a coloration of said at least one keratin fiber is achieved without an oxidizing agent.

2. A process according to claim 1, in said compounds and salts having formula (I), A and the nitrogen atom, N, together form at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; $C_1$–$C_4$ alkyl groups; ($C_1$–$C_4$)alkoxy groups; ($C_1$–$C_4$)alkylthio groups; and ($C_1$–$C_4$)alkoxycarbonyl groups.

3. A process according to claim 1, wherein, in said compounds and salts having formula (II), at least one of $R_1$ and $R_2$, $R_2$ and $R_3$, $R_3$ and $R_4$, $R_5$ and $R_1$, $R_5$ and B, and $R_4$ and B form, together with the atoms to which they are attached, at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; —$OCF_3$ groups; $C_1$–$C_4$ alkyl groups; $C_1$–$C_4$ alkoxy groups; $C_1$–$C_4$ alkylthio groups; and ($C_1$–$C_4$)alkoxycarbonyl groups.

4. A process according to claim 1, wherein said at least one keratin fiber is a human keratin fiber.

5. A process according to claim 4, wherein said human keratin fiber is hair.

6. A process according to claim 1, wherein at least one of said heterocyclic rings comprises at least one heteroatom chosen from sulphur and nitrogen.

7. A process according to claim 1, wherein said at least one compound is chosen from quinones having formula (VI), quinones having formula (VII), and the cosmetically acceptable salts thereof:

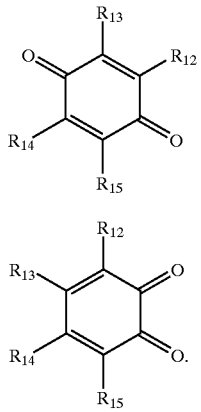

in which:

$R_{12}$ is chosen from hydrogen; halogens; sulphonic groups; and alkoxy groups;

$R_{13}$, $R_{14}$ and $R_{15}$, which may be identical or different, are each chosen from hydrogen; halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy) alkylaminoalkyl groups; alkyl-NR'R" groups, wherein R' and R", which may be identical or different, are each chosen from alkyl groups, and R' and R" may also form, together with the nitrogen atom to which they are attached, at least one ring chosen from aryl rings, 5-membered heterocycles, and 6-membered heterocycles; aryl groups; amino groups, optionally substituted with at least one group chosen from alkyl groups and hydroxyalkyl groups; and at least one of $R_{12}$ and $R_{13}$, $R_{13}$ and $R_{14}$, and $R_{14}$ and $R_{15}$ may also form, together with the atoms to which they are attached, at least one ring, optionally substituted, chosen from aryl rings; 5-membered heterocycles; and 6-membered heterocycles.

8. A process according to claim 1, wherein said at least one compound is chosen from diaminoisoindolines derivatives having formula (VIII), 3-aminoisoindolone derivatives having formula (VIII), and the cosmetically acceptable salts thereof:

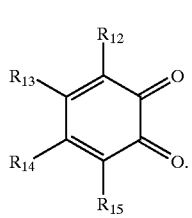

in which:

$R_{16}$ and $R_{17}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups, wherein R' and R", which may be identical or different, are each chosen from alkyl groups, and R' and R" may also form, together with the nitrogen atom to which they are attached, at least one ring chosen from aryl rings, 5-membered heterocycles, and 6-membered heterocycles;

A is chosen from oxygen and NH; and

X and Z form, together with the atoms to which they are attached, at least one ring, optionally substituted, chosen from aryl rings; 5-membered heterocycles; and 6-membered heterocycles.

9. A process according to claim 1, wherein said at least one cationic compound is chosen from:

2,3-trimethyl-3H-imidazol-1-ium iodide;

2,3,4-trimethylthiazol-3-ium iodide;

3-ethylmethylbenzothiazolium iodide;

3-methylmethylbenzothiazolium methosulphate;

1,2,3,3-tetramethyl-3H-indolium iodide;

3-ethylmethylbenzoxazolium iodide;

1,2,3-trimethyl-3H-imidazol-1-ium methosulphate;

3-(2-carboxyethyl)-2,5-dimethylbenzoxazol-3-ium bromide;

3-ethylmethylbenzothiazolium toluene-4-sulphonate;

5-chloro-3-ethyl-2-methylbenzothiazol-3-ium toluene-4-sulphonate;

1-ethyl-2-methylnaphtho[1,2-d]thiazol-1-ium toluene-4-sulphonate;

1,2,3-trimethyl-3H-benzoimidazol-1-ium tetrafluoroborate;

2-ethyl-3-methylbenzo[d]isothiazol-2-ium tetrafluoroborate;

2-methyl-3-(3-sulphonatopropyl)benzothiazol-3-ium;

3-tertbutyl-2-methylbenzothiazol-3-ium bromide;

3-(2-carboxyethyl)-2,5-dimethylbenzoxazol-3-ium bromide;

5-methoxy-2-methyl-3-(3-sulphonatopropyl) benzothiazol-3-ium;

2-methyl-1-(3-sulphonatopropyl)naphtho[1,2-d]oxazol-1-ium;

2-methyl-3-(3-sulphonatopropyl)naphtho[2,3-d]oxazol-3-ium;

1,2-dimethyinaphtho[1,2-d]thiazol-1-ium methosulphate;

3-ethyl-2,5,6-trimethylbenzoxazol-3-ium iodide;

2-methyl-1-(3-sulphonatopropyl)naphtho[1,2-d]thiazol-1-ium;

1-ethyl-2-methylnaphtho[1,2-d]thiazol-1-ium perchlorate;

2-methyl-5-phenyl-3-(3-sulphonatopropyl)benzoxazol-3-ium;

3-ethyl-6-methoxy-2-methylbenzothiazol-3-ium iodide;

5-methoxy-1,2-dimethyinaphtho[1,2-d]thiazol-1-ium iodide;

5-chloro-3-ethyl-2-methylbenzothiazol-3-ium toluene-4-sulphonate;

5,6-dimethoxy-2,3-dimethylbenzothiazol-3-ium toluene-4-sulphonate;

3-ethyl-2-methylbenzo[4,5]thieno[2,3-d]thiazol-3-ium toluene-4-sulphonate;

1-ethyl-2-methylnaphtho[1,2-d]thiazol-1-ium toluene-4-sulphonate;

5,6-dichloro-3-ethyl-2-methyl-1-(3-sulphonatobutyl)-3H-benzoimidazol-1-ium;

2,3-dimethyl-5-phenylbenzoxazol-3-ium methosulphate;
5-methoxy-1,2-dimethylbenzo[cd]indolium perchlorate;
1-butyl-2,3,3-trimethyl-3H-indolium iodide;
1,1,2,3-tetramethyl-1H-benz[e]indolium iodide; and the acid addition salts thereof.

10. A process according to claim 1, wherein said at least one cationic compound is chosen from:

1,2-dimethylquinolinium iodide;
1,2-dimethylquinolinium chloride;
1 4-dimethylquinolinium iodide;
1-ethyl-2-methylquinolinium tetrafluoroborate;
2-methyl-1-(3-sulphonatopropyl)quinolinium;
2,3-dimethylisoquinolinium iodide;
4-chloro-1,2-dimethylquinolinium methosulphate;
7-chloro-1,4-dimethylquinolinium;
1-ethyl-2,6-dimethylquinolinium iodide;
4-methoxy-1,2-dimethylquinolinium iodide;
1-ethyl-4-methylquinolinium iodide;
1,2,3,4-tetrahydropyrido[1,2-a]quinolinylium toluene-4-sulphonate;
1,1'-trimethylenebis(2,4-dimethylpyridinium) bromide;
1,1'-tetramethylenebis(2,5-dimethylpyridinium) perchlorate;
1,1'-(oxydiethylene)bis(2-methylquinolinium) perchlorate;
1,2-dimethylpyridinium methosulphate;
1,2,4-trimethylpyridinium chloride;
1,2,4,6-tetramethylpyridinium chloride;
4-methoxy-1,2,6-trimethylpyridinium perchlorate;
1-(2-hydroxyethyl)-3-methylpyridinium chloride; and the acid addition salts thereof.

11. A process according to claim 1, wherein said at least one compound is chosen from benzaldehyde; 2-monohydroxybenzaldehyde; 3-monohydroxybenzaldehyde; 4-monohydroxybenzaldehyde; 2-monomethoxybenzaldehyde; 3-monomethoxybenzaldehyde; 4-monomethoxybenzaldehyde; 2-monomethylbenzaldehyde; 3-monomethylbenzaldehyde; 4-monomethylbenzaldehyde; (2,3)-dihydroxybenzaldehyde; (2,4)-dihydroxy-benzaldehyde; (2,5)-dihydroxybenzaldehyde; (2,6)-dihydroxybenzaldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde; (3,5)-dimethoxybenzaldehyde; vanillin; isovanillin; syringaldehyde; (2,3)-dimethylbenzaldehyde; (2,4)-dimethylbenzaldehyde; (2,5)-dimethylbenzaldehyde; (2,6)-dimethylbenzaldehyde; (3,5)-dimethylbenzaldehyde; 4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaidehyde; (3,4,5)-trihydroxybenzaldehyde; (2,4,5)-trihydroxybenzaldehyde; methyl 2-formylbenzoate; methyl 3-formylbenzoate; methyl 4-formylbenzoate; 2-mono(2-hydroxyethoxy)benzaldehyde; 3-mono(2-hydroxy-ethoxy)benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxybenzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxybenzaldehyde; 3,5-dihydroxy4-methoxybenzaldehyde; 3-methoxy-2-nitrobenzaldehyde; 4-methoxy-2-nitrobenzaldehyde; 2-methoxy-3-nitrobenzaldehyde; 4-methoxy-3-nitrobenzaldehyde; (2,3,4)-trimethoxybenzaldehyde; (2,4,6)-trimethoxybenzaldehyde; (3,4,5)-trimethoxybenzaldehyde; (2,4,5)-trimethoxybenzaldehyde; 5-nitrovanillin; (2,4)-dinitrobenzaldehyde; (2,6)-dinitrobenzaldehyde; pentamethylbenzaldehyde; 4-methylsulphonylbenzaldehyde; 2-monoformylphenoxyacetic acid; 3-monoformylphenoxyacetic acid; 4-monoformylphenoxyacetic acid; 4-diethylaminosalicylaldehyde; 4-(3-dimethylaminopropoxy)benzaldehyde; 2 3-dihydrobenzo(b)furan-5-carboxaldehyde; 1-naphthaldehyde; 2-naphthaldehyde; 6-carboxaldehyde-1,4-benzodioxane; 5-carboxaldehyde-1,4-benzodioxane; 2-monohydroxy-1-naphthaldehyde; 4-monohydroxy-1-naphthaldehyde; 1-monohydroxy-2-naphthaldehyde; 1-(4-formylphenyl)imidazole; 4-pyrrolidinobenzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido(3,2,1-IJ)quinoline-9-carbaldehyde; 4-dimethylamino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldehyde; pyridine-3-monocarboxaldehyde; pyridine-4-monocarboxaldehyde; 5-formyl-6-methyluracil; pyridoxal; quinoline-2-monocarboxaldehyde; quinoline-3-monocarboxaldehyde; quinoline-4-monocarboxaldehyde; 8-hydroxyquinoline-2-carboxaldehyde; 2-furaldehyde; 3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

12. A process according to claim 1, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis (dimethylamino)benzil; camphoroquinone; cyclohexane-1, 2-dione; isatin; N-methylisatin; 4-monomethylisatin; 5-monomethylisatin; 6-monomethylisatin; 7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin;

5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxyoxindole; 5-monochlorooxindole; and 6-monochlorooxindole.

13. A process according to claim 1, wherein said at least one compound is chosen from 1,4-naphthoquinone; spinulosin; atromentin; aurentioglycocladin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone; 3,5-dihydroxy-1,4-naphthoquinone; 2,5-dihydroxy-1,4-naphthoquinone; 2-methoxy-5-hydroxy-1,4-naphthoquinone; 3-methoxy-5-hydroxy-1,4-naphthoquinone; (1,4)-naphthoquinone; (1,2)-naphthoquinone; 4,5-dimethoxy-1,2-benzoquinone; phenanthrenequinone; and (1,2)-naphthoquinone-4-sulphonic acid.

14. A process according to claim 1, wherein said at least one compound chosen from 3-imino-3H-isoindolylamine; 3-imino4-methyl-3H-isoindol-1-ylamine; 3-imino4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluoroethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1H-isoindol-4-sulphonic acid; 3-imino-7-chloro-3H-isoindol-1-ylamine; 3-imino-5-methyl-3H-isoindol-1-ylamine; 3-imino-5-ethyl-3H-isoindol-1-ylamine; 3-imino-5-tert-butyl-3H-isoindol-1-ylamine; 3-imino-5-amino-3H-isoindol-1-ylamine; N-(1-amino-3-imino-3H-isoindol-5-yl)acetamide; 3-imino-5-nitro-3H-isoindol-1-ylamine; 3-imino-5-fluoro-3H-isoindol-1-ylamine; 3-imino-5-chloro-3H-isoindol-1-ylamine; 3-imino-5-methylsulphanyl-3H-isoindol-1-ylamine; 3-imino-5-methoxy-3H-isoindol-1-ylamine; 3-imino-5-ethoxy-3H-isoindol-1-ylamine; 3-imino-5-propoxy-3H-isoindol-1-ylamine; 3-imino-5-isopropoxy-3H-isoindol-1-ylamine; 3-imino-5-butoxy-3H-isoindol-1-ylamine; 3-imino-5-isobutoxy-3H-isoindol-1-ylamine; 3-imino-5-tert-butoxy-3H-isoindol-1-ylamine; 3-imino-5-(2,2,2-trifluoromethyl)-3H-isoindol-1-ylamine; 3-imino-5-(2,2,2-trifluoroethoxy)-3H-isoindol-1-ylamine; 3-imino-5-methanesulphonyl-3H-isoindol-1-ylamine; 3-imino-5,6-dimethyl-3H-isoindol-1-ylamine; 3-imino-5,6-diethyl-3H-isoindol-1-ylamine; 3-imino-5,6-dimethoxy-3H-isoindol-1-ylamine; 3-imino-5,6-diethoxy-3H-isoindol-1-ylamine; 3-imino-5,6-dibutoxy-3H-isoindol-1-ylamine; 3-imino-5,6-bis(trifluoromethyl)-3H-isoindol-1-ylamine; 3-imino-5,6-dichloro-3H-isoindol-1-ylamine; 5,6-bis(ethoxymethyl)-3-imino-3H-isoindol-1-ylamine; 3-amino-1-imino-1H-isoindol-4,7-diol; 4,7-dichloro-3-imino-3H-isoindol-1-ylamine; 4,5,7-trichloro-3-imino-N6,N6-dimethyl-3H-isoindol-1,6-diamine; 4,5,6,7-tetrachloro-3-imino-3H-isoindol-1-ylamine; 4,5,6,7-tetrafluoro-3-imino-3H-isoindol-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7-imino-7H-pyrrolo[3,4-b]pyrid-5-ylamine; 7-imino-7H-pyrrolo[3,4-b]pyrazin-5-ylamine; 7-imino-2,3-dimethyl-7H-pyrrolo[3,4-b]pyrazin-5-ylamine; 7-imino-7H-[1,4]dithiino[2,3-c]pyrrol-5-ylamine; 7-imino-2,3-dimethyl-7H-[1,4]dithiino[2,3-c]pyrrol-5-ylamine; 7-imino-2,3-dihydro-7H-[1,4]dithiino[2,3-c]pyrrol-5-ylamine; 7-imino-2-methyl-2,3-dihydro-7H-[1,4]dithiino[2,3-c]pyrrol-5-ylamine; 3-aminoisoindol-1-one; 3-amino-7-methylisoindol-1-one; 3-amino-7-hydroxymethylisoindol-1-one; 3-amino-7-chloroisoindol-1-one; 3-amino-4-chloroisoindol-1-one; 3-amino-1-oxo-1H-isoindol4-sulphonic acid; 3-amino4-nitroisoindol-1-one; 3-amino-6-nitroisoindol-1-one; 3-amino-6-methylisoindol-1-one; 3-amino-6-chloroisoindol-1-one; 3-amino-6-bromoisoindol-1-one; 3-amino-6-methylsulphanylisoindol-1-one; 3-amino-6-methoxyisoindol-1-one; 3-amino-5-chloroisoindol-1-one; 3-amino-5-fluoroisoindol-1-one; 3-amino-5-methoxyiso-1indol-1-one; 3-amino-5-nitroisoindol-1-one; ethyl 3-amino-1-oxo-1H-isoindole-5-carboxylate; 3-amino-5,6-dichloroisoindol-1-one; 3-amino-5,6-dibromoisoindol-1-one; 3-amino-4,7-dichloroisoindol-1-one; 3-amino4,5,7-trichloroisoindol-1-one; 3-amino-4,5,6,7-tetrachloroisoindol-1-one; 3-amino-4,5,7-trichloro-6-methylsulphanylisoindol-1-one; 3-amino-4,5,6,7-tetrabromoisoindol-1-one; 3-amino-4,5,6,7-tetrafluoroisoindol-1-one; 3-methylaminoisoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-1-one; 5-aminopyrrolo[3,4-b]pyrid-7-one; 7-aminopyrrolo[3,4-b]pyrazin-5-one; 7-amino-2-methylpyrrolo[3,4-b]pyrazin-5-one; 7-amino-2,3-dimethylpyrrolo[3,4-b]pyrazin-5-one; 7-amino-2,3-dihydro[1,4]dithiino[2,3-c]pyrrol-5-one; 3-imino-2-methyl-2,3-dihydroisoindol-1-one; 3-imino-2-ethyl-2,3-dihydroisoindol-1-one; 3-imino-2-propyl-2,3-dihydroisoindol-1-one; 2-hydroxymethyl-3-imino-2,3-dihydroisoindol-1-one; 2-(2-hydroxyethyl)-3-imino-2,3-dihydroisoindol-1-one; 2-(1-imino-3-oxo-1,3-dihydroisoindol-2-yl)ethane sulphonic acid; 3-(1-imino-3-oxo-1,3-dihydroisoindol-2-yl)propionic acid; 2-(3-hydroxypropyl)-3-imino-2,3-dihydroisoindol-1-one; and 5-imino-6-methyl-5,6-dihydropyrrolo[3,4-b]pyridin-7-one.

15. A process according to claim 1, wherein said cosmetically acceptable salts are chosen from hydrochlorides; sulphates; hydrobromides; and tartrates.

16. A process according to claim 1, wherein said at least one cationic compound is chosen from 3-ethylmethylbenzothiazolium iodide; 1,2,3,3-tetramethyl-3H-indolium iodide; 3-ethylmethylbenzoxazolium iodide; 1,2-dimethylquinolinium iodide; 5-chloro-3-ethyl-2-methylbenzothiazolium iodide; and 2-methyl-1-(3-sulphopropyl)naphtho[1,2-d]thiazolium betaine.

17. A process according to claim 1, wherein said at least one compound is chosen from 1,4-naphthoquinone; isatin; N-methylisatin; 3-imino-3H-isoindol-1-ylamine; 4-dimethylaminobenzaldehyde; and 4-dimethylaminonaphthaldehyde.

18. A process according to claim 1, wherein said at least one cationic compound is present in said composition in a concentration ranging from 0.01% to 10% by weight relative to the total weight of said composition.

19. A process according to claim 18, wherein said at least one cationic compound is present in said composition in a concentration ranging from 0.05% to 5% by weight relative to the total weight of said composition.

20. A process according to claim 1, wherein said at least one compound is present in said composition in a concentration ranging from 0.01% to 10% by weight relative to the total weight of said composition.

21. A process according to claim 2, wherein said at least one compound is present in said composition in a concentration ranging from 0.05% to 5% by weight relative to the total weight of said composition.

22. A composition for dyeing at least one keratin fiber comprising:
  (a) at least one cationic compound chosen from:
    (1) compounds having formula (1) and the cosmetically acceptable salts thereof:

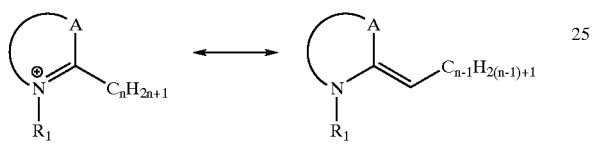

(I)

in which:
  n is an integer ranging from 1 to 4;
  $R_1$ is chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy)alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;
  A and the nitrogen atom, N, together form at least one hydrocarbon-based ring, optionally substituted, chosen from unsaturated rings comprising 5 atoms; unsaturated rings comprising 6 atoms; aromatic rings comprising 5 atoms; and aromatic rings comprising 6 atoms; wherein said at least one hydrocarbon-based ring may be interrupted by at least one atom chosen from nitrogen, oxygen and sulfur; it being possible for said at least one hydrocarbon-based ring to be fused with at least one ring chosen from unsubstituted aromatic rings and substituted aromatic rings; and
  A is chosen from carbon, optionally substituted; nitrogen, optionally substituted; oxygen; and sulfur; and
  (2) compounds having formula (II) and the cosmetically acceptable salts thereof:

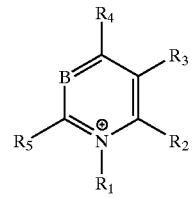

(II)

wherein:
  $R_1$, $R_2$, $R_3$, $R_4$, and $R_5$, which may be identical or different, are each chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy)alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;
  B is chosen from —CH— groups and nitrogen;
  at least one of $R_1$ and $R_2$, $R_2$ and $R_3$, $R_3$ and $R_4$, $R_5$ and $R_1$, $R_5$ and B, and $R_4$ and B may also form, together with the atoms to which they are attached, at least one hydrocarbon-based ring, optionally substituted, chosen from 5-membered unsaturated rings; 6-membered unsaturated rings; 5-membered aryl rings; 6-membered aryl rings; 5-membered heterocycles; and 6-membered heterocycles; wherein said at least one hydrocarbon-based ring may be interrupted by at least one atom chosen from nitrogen and sulfur; and
(b) at least one compound chosen from:
  (1) aldehydes having formula (III) and the cosmetically acceptable salts thereof:

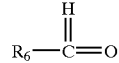

(III)

in which:
  $R_6$ is chosen from groups having formula (III A):

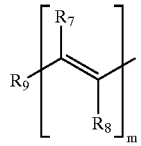

(III A)

in which:
  $R_7$ and $R_8$, which may be identical or different, are each chosen from hydrogen; alkyl. groups; monohydroxyalkyl groups; polyhydroxyalkyl groups; alkylhydroxyalkyl groups; alkoxy groups;
  —$CF_3$ groups; and —$OCF_3$ groups;
  $R_7$ and $R_8$, which may be identical or different, may also form, together with the atoms to which they are attached, at least one, ring, optionally substituted, chosen from aryl rings; 5-membered heterocyclic rings; and 6-membered heterocyclic rings;

m is an integer ranging from 0 to 3; and $R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;

(2) ketones chosen from ketones having formula (IV), ketones having formula (V), and the cosmetically acceptable salts thereof:

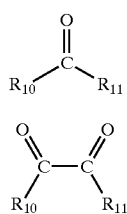

(IV)

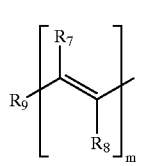

(V)

in which:

$R_{10}$ is chosen from groups having formula (III A):

(III A)

in which:

$R_7$ and $R_8$, which may be identical or different, are each chosen from hydrogen; alkyl groups; monohydroxyalkyl groups; polyhydroxyalkyl groups; alkylhydroxyalkyl groups; alkoxy groups;

—$CF_3$ groups; and —$OCF_3$ groups;

$R_7$ and $R_8$, which may be identical or different, may also form, together with the atoms to which they are attached, at least one ring, optionally substituted, chosen from aryl rings; 5-membered heterocyclic rings; and 6-membered heterocyclic rings;

m is an integer ranging from 0 to 3;

$R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;

$R_{11}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and $R_{10}$ and $R_{11}$ may also form, together with the atoms to which they are attached, at least one ring, optionally substituted, chosen from 5-membered aryl rings; 6-membered aryl rings; and heterocyclic rings; it being possible for said at least one ring itself to be attached to at least one additional ring, optionally substituted, chosen from 5-membered aryl rings, 6-membered aryl rings and heterocyclic rings comprising at least one heteroatom;

(3) quinones and the cosmetically acceptable salts thereof;

(4) diiminoisoindoline derivatives and the cosmetically acceptable salts thereof; and (5) 3-aminoisoindolone derivatives and the cosmetically acceptable salts thereof;

with the proviso that said composition does not comprise an oxidizing agent.

23. A composition according to claim 22, wherein, in said compounds and having formula (I), A and the nitrogen atom, N, together form at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; $C_1$–$C_4$ alkyl groups; ($C_1$–$C_4$)alkoxy groups; ($C_1$–$C_4$)alkylthio groups; and ($C_1$–$C_4$)alkoxycarbonyl groups.

24. A composition according to claim 22, wherein, in said compounds and salts having formula (II), at least one of $R_1$ and $R_2$, $R_2$ and $R_3$, $R_3$ and $R_4$, $R_5$ and $R_1$, $R_5$ and B, and $R_4$ and B form, together with the atoms to which they are attached, at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; —$OCF_3$ groups; $C_1$–$C_4$ alkyl groups; $C_1$–$C_4$ alkoxy groups; $C_1$–$C_4$ alkylthio groups; and ($C_1$–$C_4$)alkoxycarbonyl groups.

25. A composition according to claims 22, wherein said at least one keratin fiber is a human keratin fiber.

26. A composition according to claim 25, wherein said human keratin fiber is hair.

27. A composition according to claim 22, wherein at least one of said heterocyclic rings comprises at least one heteroatom chosen from sulphur and nitrogen.

28. A composition according to claim 22, further comprising at least one medium suitable for dyeing.

29. A composition according to claim 22, wherein said at least one compound is chosen from quinones having formula (VI), quinones having formula (VII), and the cosmetically acceptable salts thereof:

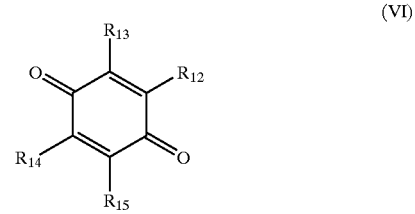

(VI)

-continued

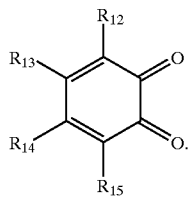
(VII)

in which:
R$_{12}$ is chosen from hydrogen; halogens; sulphonic groups; and alkoxy groups;
R$_{13}$, R$_{14}$ and R$_{15}$, which may be identical or different, are each chosen from hydrogen; halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy)alkylaminoalkyl groups; alkyl-NR'R" groups, wherein R' and R", which may be identical or different, are each chosen from alkyl groups, and R' and R" may also form, together with the nitrogen atom to which they are attached, at least one ring chosen from aryl rings, 5-membered heterocycles, and 6-membered heterocycles; aryl groups; amino groups, optionally substituted with at least one group chosen from alkyl groups and hydroxyalkyl groups; and
at least one of R$_{12}$ and R$_{13}$, R$_{13}$ and R$_{14}$, and R$_{14}$ and R$_{15}$ may also form, together with the atoms to which they are attached, at least one ring, optionally substituted, chosen from aryl rings; 5-membered heterocycles; and 6-membered heterocycles.

30. A composition according to claim 22, wherein said at least one compound is chosen from diaminoisoindolines derivatives having formula (VIII), 3-aminoisoindolone derivatives having formula (VIII), and the cosmetically acceptable salts thereof:

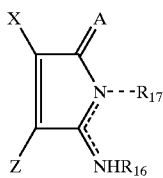
(VIII)

in which:
R$_{16}$ and R$_{17}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups, wherein R' and R" which may be identical or different, are each chosen from alkyl groups, and R' and R" may also form, together with the nitrogen atom to which they are attached, at least one ring chosen from aryl rings, 5-membered heterocycles, and 6-membered heterocycles;
A is chosen from oxygen and NH; and
X and Z form, together with the atoms to which they are attached, at least one ring, optionally substituted, chosen from aryl rings; 5-membered heterocycles; and 6-membered heterocycles.

31. A composition according to claim 22, composition having a pH ranging from 2 to 11.

32. A composition according to claim 31, wherein said pH ranges from 5 to 10.

33. A composition according to claim 22, wherein said at least one cationic compound is chosen from:
1,2,3-trimethyl-3H-imidazol-1-ium iodide;
2,3,4-trimethylthiazol-3-ium iodide;
3-ethylmethylbenzothiazolium iodide;
3-methylmethylbenzothiazolium methosulphate;
1,2,3,3-tetramethyl-3H-indolium iodide;
3-ethylmethylbenzoxazolium iodide;
1,2,3-trimethyl-3H-imidazol-1-ium methosulphate;
3-(2-carboxyethyl)-2,5-dimethylbenzoxazol-3-ium bromide;
3-ethylmethylbenzothiazolium toluene-4-sulphonate;
5-chloro-3-ethyl-2-methylbenzothiazol-3-ium toluene-4-sulphonate;
1-ethyl-2-methylnaphtho[1,2-d]thiazol-1-ium toluene-4-sulphonate;
1,2,3-trimethyl-3H-benzoimidazol-1-ium tetrafluoroborate;
2-ethyl-3-methylbenzo[d]isothiazol-2-ium tetrafluoroborate;
2-methyl-3-(3-sulphonatopropyl)benzothiazol-3-ium;
3-tertbutyl-2-methylbenzothiazol-3-ium bromide;
3-(2-carboxyethyl)-2,5-dimethylbenzoxazol-3-ium bromide;
5-methoxy-2-methyl-3-(3-sulphonatopropyl)benzothiazol-3-ium;
2-methyl-1-(3-sulphonatopropyl)naphtho[1,2-d]oxazol-1-ium;
2-methyl-3-(3-sulphonatopropyl)naphtho[2,3-d]oxazol-3-ium;
2,5,6-trimethyl-3-(3-sulphonatopropyl)thieno[2,3-d]thiazol-3-ium;
1-ethyl-2-methylnaphtho[1,2-d]oxazol-1-ium perchlorate;
1,2-dimethyinaphtho[1,2-d]thiazol-1-ium methosulphate;
3-ethyl-2,5,6-trimethylbenzoxazol-3-ium iodide;
2-methyl-1-(3-sulphonatopropyl)naphtho[1,2-d]thiazol-1-ium;
1-ethyl-2-methylnaphtho[1,2-d]thiazol-1-ium perchlorate;
2-methyl-5-phenyl-3-(3-sulphonatopropyl)benzoxazol-3-ium;
3-ethyl-6-methoxy-2-methylbenzothiazol-3-ium iodide;
5-methoxy-1,2-dimethylnaphtho[1,2-d]thiazol-1-ium iodide;
5-chloro-3-ethyl-2-methylbenzothiazol-3-ium toluene-4-sulphonate;
5,6-dimethoxy-2,3-dimethylbenzothiazol-3-ium toluene-4-sulphonate;
3-ethyl-2-methylbenzo[4,5]thieno[2,3-d]thiazol-3-ium toluene-4-sulphonate;
1-ethyl-2-methylnaphtho[1,2-d]thiazol-1-ium toluene4-sulphonate;
5,6-dichloro-3-ethyl-2-methyl-1-(3-sulphonatobutyl)-3H-benzoimidazol-1-ium;
2,3-dimethyl-5-phenylbenzoxazol-3-ium methosulphate;
5-methoxy-1,2-dimethylbenzo[cd]indolium perchlorate;
1-butyl-2,3,3-trimethyl-3H-indolium iodide;

1,1,2,3-tetramethyl-1H-benz[e]indolium iodide;
and the acid addition salts thereof.

34. A composition according to claim 22, wherein said at least one cationic compound is chosen from:

1,2-dimethylquinolinium iodide;
1,2-dimethylquinolinium chloride;
1,4-dimethylquinolinium iodide;
1-ethyl-2-methylquinolinium tetrafluoroborate;
2-methyl-1-(3-sulphonatopropyl)quinolinium;
2,3-dimethylisoquinolinium iodide;
4-chloro-1,2-dimethylquinolinium methosulphate;
7-chloro-1,4-dimethylquinolinium;
1-ethyl-2,6-dimethylquinolinium iodide;
4-methoxy-1,2-dimethylquinolinium iodide;
1-ethyl-4-methylquinolinium iodide;
1,2,3,4-tetrahydropyrido[1,2-a]quinolinylium toluene-4-sulphonate;
1,1'-trimethylenebis(2,4-dimethylpyridinium)bromide;
1,1'-tetramethylenebis(2,5-dimethylpyridinium) perchlorate;
1,1'-(oxydiethylene)bis(2-methylquinolinium) perchlorate;
1,2-dimethylpyridinium methosulphate;
1,2,4-trimethylpyridinium chloride;
1,2,4,6-tetramethylpyridinium chloride;
4-methoxy-1,2,6-trimethylpyridinium perchlorate;
1-(2-hydroxyethyl)-3-methylpyridinium chloride; and the acid addition salts thereof.

35. A composition according to claim 22, wherein said at least one compound is chosen from benzaldehyde; 2-monohydroxybenzaldehyde; 3-monohydroxybenzaldehyde; 4-monohydroxybenzaldehyde; 2-monomethoxybenzaldehyde; 3-monomethoxybenzaldehyde; 4-monomethoxybenzaldehyde; 2-monomethylbenzaldehyde; 3-monomethylbenzaldehyde; 4-monomethylbenzaldehyde; (2,3)-dihydroxybenzaldehyde; (2,4)-dihydroxybenzaldehyde; (2,5)-dihydroxybenzaldehyde; (2,6)-dihydroxybenzaldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde; (3,5)-dimethoxybenzaldehyde; vanillin; isovanillin; syringaldehyde; (2,3)-dimethylbenzaldehyde; (2,4)-dimethylbenzaldehyde; (2,5)-dimethylbenzaldehyde; (2,6)-dimethylbenzaldehyde; (3,5)-dimethylbenzaldehyde; 4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaldehyde; (3,4,5)-trihydroxybenzaldehyde; (2,4,5)-trihydroxybenzaldehyde; methyl 2-formylbenzoate; methyl 3-formylbenzoate; methyl 4-formylbenzoate; 2-mono(2-hydroxyethoxy)benzaldehyde; 3-mono(2-hydroxyethoxy)benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxybenzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxybenzaldehyde; 3,5-dihydroxy-4-methoxybenzaldehyde; 3-methoxy-2-nitrobenzaldehyde; 4-methoxy-2-nitrobenzaldehyde; 2-methoxy-3-nitrobenzaldehyde; 4-methoxy-3-nitrobenzaldehyde; (2,3,4)-trimethoxybenzaldehyde; (2,4,6)-trimethoxybenzaldehyde; (3,4,5)-trimethoxybenzaldehyde; (2,4,5)-trimethoxybenzaidehyde; 5-nitrovanillin; (2,4)-dinitrobenzaldehyde; (2,6)-dinitrobenzaldehyde; pentamethylbenzaldehyde; 4-methylsulphonylbenzaldehyde; 2-monoformylphenoxyacetic acid; 3-monoformylphenoxyacetic acid; 4-monoformylphenoxyacetic acid; 4-diethylaminosalicylaldehyde; 4-(3-dimethylaminopropoxy)benzaldehyde; 2,3-dihydrobenzo(b)furan-5-carboxaldehyde; 1-naphthaldehyde; 2-naphthaldehyde; 6-carboxaldehyde-1,4-benzodioxane; 5-carboxaldehyde-1,4-benzodioxane; 2-monohydroxy-1-naphthaldehyde; 4-monohydroxy-1-naphthaldehyde; 1-monohydroxy-2-naphthaldehyde; 1-(4-formylphenyl) imidazole; 4-pyrrolidino-benzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido(3,2,1-IJ)quinoline-9-carbaldehyde; 4-dimethylamino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldehyde; pyridine-3-monocarboxaldehyde; pyridine-4-monocarboxaldehyde; 5-formyl-6-methyluracil; pyridoxal; quinoline-2-monocarboxaldehyde; quinoline-3-monocarboxaldehyde; quinoline4-monocarboxaldehyde; 8-hydroxyquinoline-2-carboxaldehyde; 2-furaldehyde; 3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

36. A composition according to claim 22, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis(dimethylamino)benzil; camphoroquinone; cyclohexane-1,2-dione; isatin; N-methylisatin; 4-monomethylisatin; 5-monomethylisatin; 6-monomethylisatin; 7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin;

5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidihetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxy-oxindole; 5-monochlorooxindole; and 6-monochlorooxindole.

37. A composition according to claim 22, wherein said at least one compound is chosen from 1,4-naphthoquinone; spinulosin; atromentin; aurentioglycociadin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone; 3,5-dihydroxy-1,4-naphthoquinone; 2,5-dihydroxy-1,4-naphthoquinone; 2-methoxy-5-hydroxy-1,4-naphthoquinone; 3-methoxy-5-hydroxy-1,4-naphthoquinone; (1,4)-naphthoquinone; (1,2)-naphthoquinone; 4,5-dimethoxy-1,2-benzoquinone; phenanthrenequinone; and (1,2)-naphthoquinone-4-sulphonic acid.

38. A composition according to claim 22, wherein said at least one compound is chosen from 3-imino-3H-isoindolylamine; 3-imino4-methyl-3H-isoindol-1-ylamine; 3-imino-4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluoroethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1H-isoindol-4-sulphonic acid; 3-imino-7-chloro-3H-isoindol-1-ylamine; 3-imino-5-methyl-3H-isoindol-1-ylamine; 3-imino-5-ethyl-3H-isoindol-1-ylamine; 3-imino-5-tert-butyl-3H-isoindol-1-ylamine; 3-imino-5-amino-3H-isoindol-1-ylamine; N-(1-amino-3-imino-3H-isoindol-5-yl)acetamide; 3-imino-5-nitro-3H-isoindol-1-ylamine; 3-imino-5-fluoro-3H-isoindol-1-ylamine; 3-imino-5-chloro-3H-isoindol-1-ylamine; 3-imino-5-methylsulphanyl-3H-isoindol-1-ylamine; 3-imino-5-methoxy-3H-isoindol-1-ylamine; 3-imino-5-ethoxy-3H-isoindol-1-ylamine; 3-imino-5-propoxy-3H-isoindol-1-ylamine; 3-imino-5-isopropoxy-3H-isoindol-1-ylamine; 3-imino-5-butoxy-3H-isoindol-1-ylamine; 3-imino-5-isobutoxy-3H-isoindol-1-ylamine; 3-imino-5-tert-butoxy-3H-isoindol-1-ylamine; 3-imino-5-(2,2,2-trifluoromethyl)-3H-isoindol-1-ylamine; 3-imino-5-(2,2,2-trifluoroethoxy)-3H-isoindol-1-ylamine; 3-imino-5-methanesulphonyl-3H-isoindol-1-ylamine; 3-imino-5,6-dimethyl-3H-isoindol-1-ylamine; 3-imino-5,6-diethyl-3H-isoindol-1-ylamine; 3-imino-5,6-dimethoxy-3H-isoindol-1-ylamine; 3-imino-5,6-diethoxy-3H-isoindol-1-ylamine; 3-imino-5,6-dibutoxy-3H-isoindol-1-ylamine; 3-imino-5,6-bis(trifluoromethyl)-3H-isoindol-1-ylamine; 3-imino-5,6-di-chloro-3H-isoindol-1-ylamine; 5,6-bis(ethoxymethyl)3-imino-3H-isoindol-1-ylamine; 3-amino-1-imino-1H-isoindol4,7-diol; 4,7-dichloro-3-imino-3H-isoindol-1-ylamine; 4,5,7-trichloro-3-imino-N6,N6-dimethyl-3H-isoindol-1,6-diamine; 4,5,6,7-tetrachloro-3-imino-3H-isoindol-1-ylamine; 4,5,6,7-tetrafluoro-3-imino-3H-isoindol-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7-imino-7H-pyrrolo[3,4-b]pyrid-5-ylamine; 7-imino-7H-pyrrolo[3,4-b]pyrazin-5-ylamine; 7-imino-2,3-dimethyl-7H-pyrrolo[3,4-b]pyrazin-5-ylamine; 7-imino-7H-[1,4]dithiino[2,3-c]pyrrol-5-ylamine; 7-imino-2,3-dimethyl-7H-[1,4]dithiino[2,3-c]pyrrol-5-ylamine; 7-imino-2,3-dihydro-7H-[1,4]dithiino[2,3-c]pyrrol-5-ylamine; 7-imino-2-methyl-2,3-dihydro-7H-[1,4]dithiino[2,3-c]pyrrol-5-ylamine; 3-aminoisoindol-1-one; 3-amino-7-methylisoindol-1-one; 3-amino-7-hydroxymethylisoindol-1-one; 3-amino-7-chloroisoindol-1-one; 3-amino-4-chloroisoindol-1-one; 3-amino-1-oxo-1H-isoindol-4-sulphonic acid; 3-amino-4-nitroisoindol-1-one; 3-amino-6-nitroisoindol-1-one; 3-amino-6-methylisoindol-1-one; 3-amino-6-chloroisoindol-1-one; 3-amino-6-bromoisoindol-1-one; 3-amino-6-methylsulphanylisoindol-1-one; 3-amino-6-methoxyisoindol-1-one; 3-amino-5-chloroisoindol-1-one; 3-amino-5-fluoroisoindol-1-one; 3-amino-5-methoxyisoindol-1-one; 3-amino-5-nitroisoindol-1-one; ethyl 3-amino-1-oxo-1H-isoindole-5-carboxylate; 3-amino-5,6-dichloroisoindol-1-one; 3-amino-5,6-dibromoisoindol-1-one; 3-amino-4,7-dichloroisoindol-1-one; 3-amino-4,5,7-trichloroisoindol-1-one; 3-amino-4,5,6,7-tetrachloroisoindol-1-one; 3-amino-4,5,7-trichloro-6-methylsulphanylisoindol-1-one; 3-amino-4,5,6,7-tetrabromoisoindol-1-one; 3-amino-4,5,6,7-tetrafluoroisoindol-1-one; 3-methylaminoisoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-one; 5-aminopyrrolo[3,4-b]pyrid-7-one; 7-aminopyrrolo[3,4-b]pyrazin-5-one; 7-amino-2-methylpyrrolo[3,4-b]pyrazin-5-one; 7-amino-2,3-dimethylpyrrolo[3,4-b]pyrazin-5-one; 7-amino-2,3-dihydro[1,4]dithiino[2,3-c]pyrrol-5-one; 3-imino-2-methyl-2,3-dihydroisoindol-1-one; 3-imino-2-ethyl-2,3-dihydroisoindol-1-one; 3-imino-2-propyl-2,3-dihydroisoindol-1-one; 2-hydroxymethyl-3-imino-2,3-dihydroisoindol-1-one; 2-(2-hydroxyethyl)-3-imino-2,3-dihydroisoindol-1-one; 2-(1-imino-3-oxo-1,3-dihydroisoindol-2-yl)ethane sulphonic acid; 3-(1-imino-3-oxo-1,3-dihydroisoindol-2-yl)propionic acid; 2-(3-hydroxypropyl)-3-imino-2,3-dihydroisoindol-1 one; and 5-imino-6-methyl-5,6-dihydropyrrolo[3,4-b]pyridin-7-one.

39. A composition according to claim 22, wherein said cosmetically acceptable salts are chosen from hydrochlorides; sulphates; hydrobromides; and tartrates.

40. A composition according to claim 22, wherein said at least one cationic compound is chosen from 3-ethylmethylbenzothiazolium iodide; 1,2,3,3-tetramethyl-3H-indolium iodide; 3-ethylmethylbenzoxazolium iodide; 1,2-dimethylquinolinium iodide; 5-chloro-3-ethyl-2-methylbenzothiazolium iodide; and 2-methyl-1-(3-sulphopropyl)naphtho[1,2-d]thiazolium betaine.

41. A composition according to claim 22, wherein said at least one compound is chosen from naphthoquinone; isatin; N-methylisatin; 3-imino-3H-isoindol-1-ylamine; 4-dimethylaminobenzadehyde; and 4-dimethylaminobenzaldehyde.

42. A composition according to claim 22, wherein said at least one cationic compound is present in said composition in a concentration ranging from 0.01% to 10% by weight relative to the total weight of said composition.

43. A composition according to claim 42, wherein said at least one cationic compound is present in said composition in a concentration ranging from 0.05% to 5% by weight relative to the total weight of said composition.

44. A composition according to claim 22, wherein said at least one compound is present in said composition in a concentration ranging from 0.01% to 10% by weight relative to the total weight of said composition.

45. A composition according to claim 44, wherein said at least one compound is present in said composition in a concentration ranging from 0.05% to 5% by weight relative to the total weight of said composition.

46. A composition according to claim 22, further comprising at least one fatty amide.

47. A composition according to claim 46, wherein said at least one fatty amide is chosen from monoethanolamides of acids derived from copra; monoethanolamides of lauric acid; monoethanolamides of oleic acid; diethanolamides of acids derived from copra; diethanolamides of lauric acid; and diethanolamides of oleic acid.

48. A composition according to claim 46, wherein said at least one fatty amide is present in a concentration ranging from 0.05% to 10%. by weight relative to the total weight of said composition.

49. A composition according to claim 22, further comprising at least one surfactant.

50. A composition according to claim 49, wherein said at least one surfactant is chosen from anionic surfactants; cationic surfactants; nonionic surfactants; amphoteric surfactants; and zwitterionic surfactants.

51. A composition according to claim 49, wherein said at least one surfactant is present in a concentration ranging from about 0.1% to about 50% by weight relative to the total weight of said composition.

52. A composition according to claim 51, wherein said at least one surfactant is present in a concentration ranging from about 1% to about 20% by weight relative to the total weight of said composition.

53. A composition according to claim 22, further comprising at least one thickener.

54. A composition according to claim 53, wherein said at least one thickener is present in a concentration ranging from about 0.2% to about 20% by weight relative to the total weight of said composition.

55. A composition according to claim 22, further comprising at least one cosmetically acceptable adjuvant chosen from antioxidants; fragrances; sequestering agents; dispersants; hair conditioners; preserving agents; and opacifiers.

56. A composition according to claim 22, wherein said composition is in the form of a liquid, a cream or a gel.

57. A composition according to claim 28, wherein said at least one medium suitable for dyeing is an aqueous medium chosen from water and organic solvents.

58. A composition according to claim 52, wherein said organic solvents are chosen from alcohols; glycols; glycol ethers; and mixtures thereof.

59. A composition according to claim 28, wherein said at least one medium suitable for dyeing is present in a concentration ranging from 0.5% to 20% by weight relative to the total weight of said composition.

60. A multi-compartment device or dyeing kit, wherein said device or dyeing kit comprises at least two compartments, wherein:
(a) a first compartment comprises a component (A); and
(b) a second compartment comprises a component (B);
wherein said component (A) comprises a composition which comprises at least one cationic compound chosen from:

(1) compounds having formula (I) and the cosmetically acceptable salts thereof:

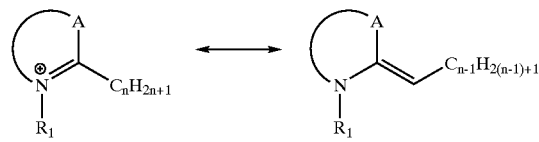

in which:
n is an integer ranging from 1 to 4;
$R_1$ is chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy) alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;
A and the nitrogen atom, N, together form at least one hydrocarbon-based ring, optionally substituted, chosen from unsaturated rings comprising 5 atoms; unsaturated rings comprising 6 atoms; aromatic rings comprising 5 atoms; and aromatic rings comprising 6 atoms; wherein said at least one hydrocarbon-based ring may be interrupted by at least one atom chosen from nitrogen, oxygen and sulfur; it being possible for said at least one hydrocarbon-based ring to be fused with at least one ring chosen from unsubstituted aromatic rings and substituted aromatic rings; and
A is chosen from carbon, optionally substituted; nitrogen, optionally substituted; oxygen; and sulfur; and
(2) compounds having formula (II) and the cosmetically acceptable salts thereof:

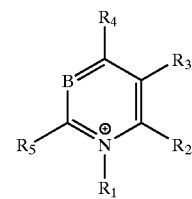

wherein:
$R_1$, $R_2$, $R_3$, $R_4$, and $R_5$, which may be identical or different, are each chosen from alkyl groups; hydroxyalkyl groups; polyhydroxyalkyl groups; alkylhydroxyalkyl groups; alkylsulfonyl groups; carboxyalkyl groups; aminoalkyl groups; (dihydroxy)alkylaminoalkyl groups; alkyl-NR'R" groups, wherein R' and R", which may be identical or different, are each chosen from linear alkyl groups comprising from 1 to 4 carbon atoms and branched alkyl groups comprising from 1 to 4 carbon atoms, and R' and R" may also form, together with the nitrogen atom to which they attached, at least one ring chosen from 5-membered aliphatic rings, 6-membered aliphatic rings, 5-membered heterocyclic rings, and 6-membered heterocyclic rings; and aryl rings;

B is chosen from —CH— groups and nitrogen;

at least one of $R_1$ and $R_2$, $R_2$ and $R_3$, $R_3$ and $R_4$, $R_5$ and $R_1$, $R_5$ and B, and $R_4$ and B may also form, together with the atoms to which they are attached, at least one hydrocarbon-based ring, optionally substituted, chosen from 5-membered unsaturated rings; 6-membered unsaturated rings; 5-membered aryl rings; 6-membered aryl rings; 5-membered heterocycles; and 6-membered heterocycles; wherein said at least one hydrocarbon-based ring may be interrupted by at least one atom chosen from nitrogen and sulfur; and wherein said component (B) comprises a composition which comprises at least one compound chosen from:

(1) aldehydes having formula (III) and the cosmetically acceptable salts thereof:

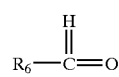

(III)

in which:

$R_6$ is chosen from groups having formula (III A):

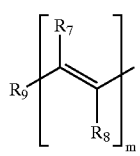

(III A)

in which:

$R_7$ and $R_8$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_7$ and $R_8$, which may be identical or different, may also form, together with the atoms to which they are attached, at least one ring, optionally substituted, chosen from aryl rings; 5-membered heterocyclic rings; and 6-membered heterocyclic rings;

m is an integer ranging from 0 to 3; and $R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered hetero-cyclic groups, optionally substituted;

(2) ketones chosen from ketones having formula (IV), ketones having formula (V), and the cosmetically acceptable salts thereof:

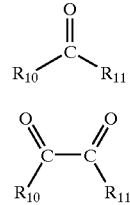

in which:

$R_{10}$ is chosen from groups having formula (III A):

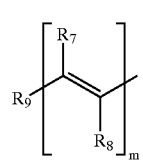

(III A)

in which:

$R_7$ and $R_8$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_7$ and $R_8$, which may be identical or different, may also form, together with the atoms to which they are attached, at least one ring, optionally substituted, chosen from aryl rings; 5-membered heterocyclic rings; and 6-membered heterocyclic rings;

m is an integer ranging from 0 to 3;

$R_9$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;

$R_{11}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and $R_{10}$ and $R_{11}$ may also form, together with the atoms to which they are attached, at least one ring, optionally substituted, chosen from 5-membered aryl rings; 6-membered aryl rings; and heterocyclic rings it being possible for said at least one ring itself to be attached to at least one additional ring, optionally substituted, chosen from 5-membered aryl rings, 6-membered aryl rings and heterocyclic rings comprising at least one heteroatom;

(3) quinones and the cosmetically acceptable salts thereof;

(4) diiminoisoindoline derivatives and the cosmetically acceptable salts thereof; and (5) 3-aminoisoindolone derivatives and the cosmetically acceptable salts thereof;

with the proviso that a coloration of said at least one keratin fiber is achieved without an oxidizing agent.

61. A multi-compartment device or dyeing kit according to claim 60, wherein, in said compounds and salts having formula (I), A and the nitrogen atom, N, together form at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; $C_1$–$C_4$ alkyl groups; ($C_1$–$C_4$)alkoxy groups; ($C_1$–$C_4$)alkylthio groups; and ($C_1$–$C_4$)alkoxycarbonyl groups.

62. A multi-compartment device or dyeing kit according to claim 60, wherein, in said compounds and salts having formula (II), at least one of $R_1$ and $R_2$, $R_2$ and $R_3$, $R_3$ and $R_4$, $R_5$ and $R_1$, $R_5$ and B, and $R_4$ and B form, together with the atoms to which they are attached, at least one hydrocarbon-based ring substituted with at least one group chosen from —$NO_2$ groups; —$NH_2$ groups; acetylamino groups; —OH groups; —$SO_3H$ groups; halogens; —$CH_3SO_2$ groups; —$CF_3$ groups; —$OCF_3$ groups; $C_1$–$C_4$ alkyl groups; $C_1$–$C_4$ alkoxy groups; $C_1$–$C_4$ alkylthio groups; and ($C_1$–$C_4$) alkoxycarbonyl groups.

63. A multi-compartment device or dyeing kit according to claim 60, wherein said cosmetically acceptable salts are chosen from hydrochlorides; sulphates; hydrobromides; and tartrates.

64. A multi-compartment device or dyeing kit according to claim 60, wherein at least one component chosen from said component (A) and said component (B) is in the form of an anhydrous composition; and wherein said device or dyeing kit comprises a third compartment comprising a cosmetically acceptable aqueous medium which is suitable for dyeing and which is intended to be mixed, before use, into at least one compartment chosen from said first compartment comprising said component (A) and said second compartment comprising said component (B).

\* \* \* \* \*

UNITED STATES PATENT AND TRADEMARK OFFICE
CERTIFICATE OF CORRECTION

PATENT NO. : 6,635,090 B1
DATED : October 21, 2003
INVENTOR(S) : Andrean et al.

It is certified that error appears in the above-identified patent and that said Letters Patent is hereby corrected as shown below:

Column 19,
In the structure for formula I between lines 37-44,

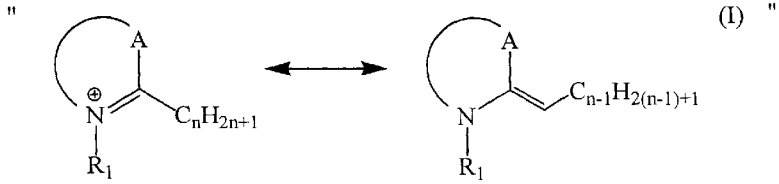

should read

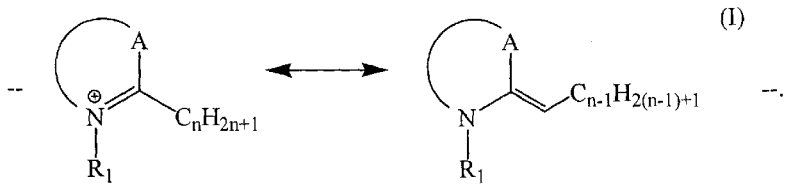

Column 21,
Line 15, "groups;.alkylhydroxyalkyl" should read -- groups; alkylhydroxyalkyl --.

Column 22,
Line 40, before "with the proviso", delete "it".
Line 42, after "claim 1,", insert -- wherein, --.
Line 52, "$R_3$and" should read -- $R_3$ and --.

Column 23,
Line 20, after the structure for formula (VII), delete the period.

Column 24,
Line 14, "2,3-trimethyl-3H-imidazol-1-ium" should
read -- 1,2,3-trimethyl-3H-imidazol-1-ium --.
Lines 43-44, after "2-methyl-3-(3-sulphonatopropyl)naptho[2,3-d] oxazol-3-ium;",
insert the following missing compounds: -- 2,5,6-trimethyl-3-(3-sulphonatopropyl)
thieno[2,3-d]thiazol-3-ium; 1-ethyl-2-methylnaphtho[1,2-d]oxazol-1-ium
perchlorate; --.
Line 45, "1,2-dimethyinaphtho[1,2-d]thiazol-1-ium" should read
-- 1,2-dimethylnaphtho[1,2-d]thiazol-1-ium --.
Line 55, "5-methoxy-1,2-dimethyinaphtho[1,2-d]thiazol-1-ium" should read
-- 5-methoxy-1,2-dimethylnaphtho[1,2-d]thiazol-1-ium --.

UNITED STATES PATENT AND TRADEMARK OFFICE
CERTIFICATE OF CORRECTION

PATENT NO. : 6,635,090 B1
DATED : October 21, 2003
INVENTOR(S) : Andrean et al.

It is certified that error appears in the above-identified patent and that said Letters Patent is hereby corrected as shown below:

Column 25,
Line 11, "1 4-dimethylquinolinium" should read -- 1,4-dimethylquinolinium --.
Line 64, "(2,4,6)-trihydroxybenzaidehyde;" should
read -- (2,4,6)-trihydroxybenzaldehyde; --.

Column 26,
Lines 10-11, "3,5-dihydroxy4-methoxybenzaldehyde;" should
read -- 3,5-dihydroxy-4-methoxybenzaldehyde; --.

Column 27,
Line 36, "3-imino4-methyl-3H-isoindol-1-ylamine;" should read
-- 3-imino-4-methyl-3H-isoindol-1-ylamine; --.
Lines 36-37, "3-imino4-tert-butyl-3H-isoindol-1-ylamine;" should read
-- 3-imino-4-tert-butyl-3H-isoindol-1-ylamine; --.
Lines 65-66, "5,6-bis(ethoxymethyl)-3-imino-3H-isoindol-1-ylamine;" should
read -- 5,6-bis(ethoxymethyl)3-imino-3H-isoindol-1-ylamine; --.

Column 28,
Line 17, "3-amino-l-oxo-1H-isoindol4-sulphonic" should read
-- 3-amino-l-oxo-1H-isoindol-4-sulphonic --.
Lines 17-18, "3-amino4-nitroisoindol-1-one;" should read -- 3-amino-4-
nitroisoindol-1-one; --.
Lines 23-24, "3-amino-5-methoxyiso-1indol-1-one;" should read -- 3-amino-5-
methoxyiso-indol-1-one; --.
Lines 27-28, "3-amino4,5,7-trichloroisoindol-1-one;" should read
-- 3-amino-4,5,7-trichloroisoindol-1-one; --.
Lines 36-37, "3-amino-6-methylpyrrolo[3,4-c]pyrid-1-1-one;" should read
-- 3-amino-6-methylpyrrolo[3,4-c]pyrid-1-one; --.

Column 29,
Line 12, "claim 2," should read -- claim 20, --.
Line 20, "formula (1)" should read -- formula (I) --.

Column 30,
Line 29, "$R_2$and $R_3$, $R_3$and $R_4$," should read -- $R_2$ and $R_3$, $R_3$ and $R_4$, --.
Line 30, "$R_5$and B," should read -- $R_5$ and B, --.
Line 61, "alkyl. groups;" should read -- alkyl groups; --.

UNITED STATES PATENT AND TRADEMARK OFFICE
CERTIFICATE OF CORRECTION

PATENT NO. : 6,635,090 B1
DATED : October 21, 2003
INVENTOR(S) : Andrean et al.

It is certified that error appears in the above-identified patent and that said Letters Patent is hereby corrected as shown below:

Column 31,
Line 1, after "at least one", delete the comma.

Column 32,
Line 23, after "compounds and", insert -- salts --.
Line 33, "R$_5$and B," should read -- R$_5$ and B, --.
Line 42, "claims 22," should read -- claim 22, --.

Column 33,
Line 7, after the structure for formula (VII), delete the period.
Line 55, "R' and R" which" should read -- R' and R", which --.
Line 66, "claim 22, composition" should read -- claim 22, said composition --.

Column 34,
Line 41, "1,2-dimethyinaphtho[1,2-d]thiazol-1-ium" methosulphate; should read -- 1,2-dimethylnaphtho[1,2-d]thiazol-1-ium methosulphate --.
Lines 60-61, "toluene4-sulphonate;" should read -- toluene-4-sulphonate; --.

Column 36,
Line 14, "(2,4,5)-trimethoxybenzaidehyde;" should read -- (2,4,5)-trimethoxybenzaldehyde; --.
Line 38, "quinoline4-monocarboxaldehyde;" should read -- quinoline-4-monocarboxaldehyde; --.

Column 37,
Lines 4-5, "1,3-dimethylhexahydro-2,4,5,6-pyrimidihetetraone;" should read -- 1,3-dimethylhexahydro-2,4,5,6-pyrimidinetetraone; --.
Line 17, "aurentioglycociadin;" should read -- aurentioglycocladin; --.
Line 34, "3-imino4-methyl-3H-isoindol-1-ylamine;" should read -- 3-imino-4-methyl-3H-isoindol-1-ylamine; --.
Lines 64-65, "3-amino-l-imino-1H-isoindol4,7-diol; should read -- 3-amino-1-imino-1H-isoindol-4,7-diol; --.

Column 38,
Lines 46-47, "2-(3-hydroxypropyl)-3-imino-2,3-dihydroisoindol-1 one;" should read -- 2-(3-hydroxypropyl)-3-imino-2,3-dihydroisoindol-1-one; --.
Line 62, "4-dimethylaminobenzadehyde;" should read -- 4-dimethylaminobenzaldehyde; --.

UNITED STATES PATENT AND TRADEMARK OFFICE
CERTIFICATE OF CORRECTION

PATENT NO. : 6,635,090 B1
DATED : October 21, 2003
INVENTOR(S) : Andrean et al.

It is certified that error appears in the above-identified patent and that said Letters Patent is hereby corrected as shown below:

Column 39,
Line 22, "10%." should read -- 10% --.
Line 53, "claim 52," should read -- claim 57, --.

Column 42,
Line 55, "rings" should read -- rings; --.

Column 43,
Line 12, "$R_3$and $R_4$," should read -- $R_3$ and $R_4$, --.
Line 13, "$R_5$and $R_1$," should read -- $R_5$ and $R_1$, --.

Signed and Sealed this

Twenty-seventh Day of January, 2004

JON W. DUDAS
*Acting Director of the United States Patent and Trademark Office*